US012617850B2

(12) United States Patent
Yang

(10) Patent No.: US 12,617,850 B2
(45) Date of Patent: May 5, 2026

(54) TREATMENT OF PD-L1-POSITIVE MELANOMA USING AN ANTI-PD-1 ANTIBODY

(71) Applicant: Bristol-Myers Squibb Company, Princeton, NJ (US)

(72) Inventor: Arvin Yang, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 412 days.

(21) Appl. No.: 17/701,436

(22) Filed: Mar. 22, 2022

(65) Prior Publication Data

US 2022/0281974 A1 Sep. 8, 2022

Related U.S. Application Data

(63) Continuation of application No. 16/430,106, filed on Jun. 3, 2019, now abandoned, which is a continuation of application No. 15/141,772, filed on Apr. 28, 2016, now abandoned.

(60) Provisional application No. 62/153,954, filed on Apr. 28, 2015.

(51) Int. Cl.

| *C07K 16/28* | (2006.01) |
| *A61K 39/395* | (2006.01) |
| *A61P 35/00* | (2006.01) |
| *G01N 33/574* | (2006.01) |
| *A61K 39/00* | (2006.01) |

(52) U.S. Cl.
CPC .......... *C07K 16/2803* (2013.01); *A61P 35/00* (2018.01); *C07K 16/2818* (2013.01); *G01N 33/5743* (2013.01); *A61K 39/395* (2013.01); *A61K 2039/505* (2013.01); *A61K 2039/507* (2013.01); *A61K 2039/545* (2013.01); *A61K 2039/55* (2013.01); *C07K 2317/21* (2013.01); *C07K 2317/56* (2013.01); *C07K 2317/565* (2013.01); *G01N 2333/70532* (2013.01)

(58) Field of Classification Search
CPC ........... A61K 39/395; A61K 39/39558; A61K 2039/505; A61K 2039/545; G01N 33/5743; G01N 33/577; A61P 35/00; C07K 2317/21; C07K 2317/56; C07K 2317/565
See application file for complete search history.

(56) References Cited

U.S. PATENT DOCUMENTS

| 5,952,199 A | 9/1999 | Davis-Smyth et al. |
| 5,977,318 A | 11/1999 | Linsley et al. |
| 6,051,227 A | 4/2000 | Allison et al. |
| 6,682,736 B1 | 1/2004 | Hanson et al. |
| 6,808,710 B1 | 10/2004 | Wood et al. |
| 6,984,720 B1 | 1/2006 | Korman et al. |
| 7,034,121 B2 | 4/2006 | Carreno et al. |
| 7,169,901 B2 | 1/2007 | Baca et al. |
| 7,297,334 B2 | 11/2007 | Baca et al. |
| 7,423,125 B2 | 9/2008 | Alitalo et al. |
| 7,488,802 B2 | 2/2009 | Collins et al. |
| 7,498,414 B2 | 3/2009 | Zhu |
| 7,595,048 B2 | 9/2009 | Honjo et al. |
| 7,605,238 B2 | 10/2009 | Korman et al. |
| 7,943,743 B2 | 5/2011 | Korman et al. |
| 7,972,596 B2 | 7/2011 | Wu et al. |
| 8,008,449 B2 | 8/2011 | Korman et al. |
| 8,034,905 B2 | 10/2011 | Kavile et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,354,509 B2 | 1/2013 | Carven et al. |
| 8,383,796 B2 | 2/2013 | Korman et al. |
| 8,609,089 B2 | 12/2013 | Langermann et al. |
| 8,686,119 B2 | 4/2014 | Rotem-Yehudar et al. |
| 8,728,474 B2 | 5/2014 | Honjo et al. |
| 8,779,105 B2 | 7/2014 | Korman et al. |
| 8,779,108 B2 | 7/2014 | Queva et al. |
| 8,900,587 B2 | 12/2014 | Carven et al. |
| 9,067,999 B1 | 6/2015 | Honjo et al. |
| 9,073,994 B2 | 7/2015 | Honjo et al. |
| 9,084,776 B2 | 7/2015 | Korman et al. |
| 9,102,725 B2 | 8/2015 | Korman et al. |
| 9,212,224 B2 | 12/2015 | Cogswell et al. |
| 9,273,135 B2 | 3/2016 | Korman et al. |
| 9,358,289 B2 | 6/2016 | Korman et al. |

(Continued)

FOREIGN PATENT DOCUMENTS

| EP | 3322731 A1 | 5/2018 |
| WO | WO-0044777 A1 | 8/2000 |

(Continued)

OTHER PUBLICATIONS

Wang et al., J Clin Pharmacol., 2009, 49(9): 1012-24.*
Ascierto, P.A., et al., "Biomarkers for Immunostimulatory Monoclonal Antibodies in Combination Strategies for Melanoma and Other Tumor Types," Clinical Cancer Research 19(5):1009-1020, American Association for Cancer Research, United States (May 2013).

(Continued)

*Primary Examiner* — Hong Sang
(74) *Attorney, Agent, or Firm* — Sterne, Kessler, Goldstein & Fox P.L.L.C.

(57) ABSTRACT

The invention provides a method of treating a melanoma comprising (i) identifying a patient having a PD-L1 positive melanoma and (ii) administering to the patient an anti-PD-1 antibody or an antigen-binding portion thereof ("an anti-PD-1 antibody monotherapy"). The methods of the invention can extend progression-free survival for over 12 months and/or reduces the tumor size at least about 10%, about 20%, about 30%, about 40%, or about 50% compared to the tumor size prior to the administration.

10 Claims, 6 Drawing Sheets

Specification includes a Sequence Listing.

(56) References Cited

U.S. PATENT DOCUMENTS

| | | | |
|---|---|---|---|
| 9,387,247 B2 | 7/2016 | Korman et al. | |
| 9,393,301 B2 | 7/2016 | Honjo et al. | |
| 9,402,899 B2 | 8/2016 | Honjo et al. | |
| 9,439,962 B2 | 9/2016 | Honjo et al. | |
| 9,492,539 B2 | 11/2016 | Korman et al. | |
| 9,492,540 B2 | 11/2016 | Korman et al. | |
| 9,683,048 B2 | 6/2017 | Freeman et al. | |
| 9,765,147 B2 * | 9/2017 | Wong | A61P 17/00 |
| 9,856,320 B2 | 1/2018 | Cogswell et al. | |
| 9,907,849 B2 | 3/2018 | Petit et al. | |
| 10,072,082 B2 * | 9/2018 | Cogswell | C07K 16/2803 |
| 10,081,681 B2 * | 9/2018 | Korman | C07K 16/2803 |
| 10,138,299 B2 | 11/2018 | Cogswell et al. | |
| 10,174,113 B2 | 1/2019 | Yang | |
| 10,221,244 B2 * | 3/2019 | Wong | A61P 15/00 |
| 10,266,594 B1 | 4/2019 | Cogswell et al. | |
| 10,266,595 B2 | 4/2019 | Cogswell et al. | |
| 10,266,596 B1 | 4/2019 | Cogswell et al. | |
| 10,308,714 B2 | 6/2019 | Cogswell et al. | |
| 10,316,090 B2 | 6/2019 | Cogswell et al. | |
| 10,316,091 B2 | 6/2019 | Cogswell et al. | |
| 10,323,092 B2 | 6/2019 | Cogswell et al. | |
| 10,323,093 B2 | 6/2019 | Cogswell et al. | |
| 10,370,446 B2 | 8/2019 | Freeman et al. | |
| 10,392,442 B2 * | 8/2019 | Coric | A61K 45/06 |
| 10,441,655 B2 | 10/2019 | Korman et al. | |
| 10,577,423 B2 | 3/2020 | Cogswell et al. | |
| 10,584,170 B2 | 3/2020 | Cogswell et al. | |
| 10,604,575 B2 | 3/2020 | Cogswell et al. | |
| 10,618,967 B2 * | 4/2020 | Wong | A61P 1/16 |
| 10,668,152 B2 * | 6/2020 | Coric | A61K 39/00 |
| 11,078,278 B2 | 8/2021 | Simon et al. | |
| 11,351,163 B2 * | 6/2022 | Basciano | A61K 45/06 |
| 2006/0110383 A1 | 5/2006 | Honjo et al. | |
| 2009/0217401 A1 | 8/2009 | Korman et al. | |
| 2012/0263677 A1 | 10/2012 | Eagle et al. | |
| 2013/0017199 A1 | 1/2013 | Langermann | |
| 2013/0309250 A1 | 11/2013 | Cogswell et al. | |
| 2014/0341917 A1 | 11/2014 | Nastri et al. | |
| 2014/0356353 A1 | 12/2014 | Queva et al. | |
| 2015/0079109 A1 | 3/2015 | Li et al. | |
| 2015/0125463 A1 | 5/2015 | Cogswell et al. | |
| 2015/0290316 A1 | 10/2015 | Graziano et al. | |
| 2016/0022814 A1 * | 1/2016 | Petit | A61P 35/00 |
| | | | 424/85.1 |
| 2016/0031990 A1 | 2/2016 | Steele et al. | |
| 2016/0075782 A1 | 3/2016 | Korman et al. | |
| 2016/0090417 A1 | 3/2016 | Cogswell et al. | |
| 2016/0222116 A1 | 8/2016 | Korman et al. | |
| 2016/0340428 A1 | 11/2016 | Yang et al. | |
| 2016/0362489 A1 | 12/2016 | Yang et al. | |
| 2016/0362495 A1 | 12/2016 | Korman et al. | |
| 2017/0051060 A1 | 2/2017 | Honjo et al. | |
| 2017/0088615 A1 | 3/2017 | Korman et al. | |
| 2017/0158776 A1 | 6/2017 | Feltquate et al. | |
| 2018/0133313 A1 * | 5/2018 | Coric | A61K 39/39558 |
| 2018/0237534 A1 * | 8/2018 | Cai | C07K 16/30 |
| 2018/0273624 A1 | 9/2018 | Cogswell et al. | |
| 2018/0282413 A1 | 10/2018 | Cogswell et al. | |
| 2018/0282414 A1 | 10/2018 | Cogswell et al. | |
| 2018/0312590 A1 | 11/2018 | Cogswell et al. | |
| 2018/0319887 A1 | 11/2018 | Cogswell et al. | |
| 2019/0092863 A1 | 3/2019 | Cogswell et al. | |
| 2019/0100589 A1 | 4/2019 | Cogswell et al. | |
| 2019/0100590 A1 | 4/2019 | Cogswell et al. | |
| 2019/0112376 A1 | 4/2019 | Cogswell et al. | |
| 2019/0112377 A1 | 4/2019 | Cogswell et al. | |
| 2019/0135920 A1 | 5/2019 | Cogswell et al. | |
| 2019/0153099 A1 | 5/2019 | Cogswell et al. | |
| 2019/0194328 A1 | 6/2019 | Yang | |
| 2020/0010549 A1 | 1/2020 | Yang | |
| 2020/0062846 A1 | 2/2020 | Honjo et al. | |
| 2020/0109204 A1 | 4/2020 | Edwards et al. | |
| 2020/0138945 A1 | 5/2020 | Korman et al. | |
| 2020/0308282 A1 | 10/2020 | Cogswell et al. | |
| 2020/0325226 A1 | 10/2020 | Edwards et al. | |
| 2021/0009697 A1 | 1/2021 | Lewis et al. | |
| 2021/0030739 A1 | 2/2021 | Basciano et al. | |
| 2021/0054063 A1 | 2/2021 | Carleton et al. | |
| 2021/0101980 A1 | 4/2021 | Seshaiyer et al. | |
| 2021/0147570 A1 | 5/2021 | Altura et al. | |
| 2021/0206854 A1 * | 7/2021 | Nathan | A61P 43/00 |
| 2022/0281974 A1 | 9/2022 | Yang | |

FOREIGN PATENT DOCUMENTS

| | | | | |
|---|---|---|---|---|
| WO | WO-2004004771 A1 | 1/2004 | | |
| WO | WO-2006121168 A1 | 11/2006 | | |
| WO | WO-2007005874 A2 | 1/2007 | | |
| WO | WO-2007113648 A2 | 10/2007 | | |
| WO | WO-2010019570 A2 | 2/2010 | | |
| WO | WO-2012122444 A1 | 9/2012 | | |
| WO | WO-2012145493 A1 | 10/2012 | | |
| WO | WO-2013014668 A1 | 1/2013 | | |
| WO | WO-2013173223 A1 * | 11/2013 | | A61K 39/395 |
| WO | WO-2015042246 A1 | 3/2015 | | |
| WO | WO-2015112900 A1 | 7/2015 | | |
| WO | WO-2015176033 A1 | 11/2015 | | |
| WO | WO-2015181331 A1 | 12/2015 | | |
| WO | WO-2016029073 A2 | 2/2016 | | |
| WO | WO-2016168716 A1 | 10/2016 | | |
| WO | WO-2016176503 A1 | 11/2016 | | |
| WO | WO-2016176504 A1 | 11/2016 | | |
| WO | WO-2017011666 A1 | 1/2017 | | |

OTHER PUBLICATIONS

Ascierto, P.A., et al., "The Additional Facet of Immunoscore: Immunoprofiling as a Possible Predictive Tool for Cancer Treatment," Journal of Translational Medicine 11:54, BioMed Central Ltd., United Kingdom, 4 pages (Mar. 2013).

Bowyer, S., et al., "Efficacy and Toxicity of Treatment with the Anti-CTLA-4 Antibody Ipilimumab in Patients with Metastatic Melanoma after Prior Anti-PD-1 Therapy," British Journal of Cancer 114(10):1084-1089, Nature Publishing Group, England (May 2016).

Brahmer, J.R., et al., "Safety and Activity of Anti-PD-L1 Antibody in Patients with Advanced Cancer," The New England Journal of Medicine 366(26):2455-2465, Massachusetts Medical Society, United States (Jun. 2012).

Condeelis, J. and Weissleder, R., "In Vivo Imaging in Cancer," Cold Spring Harbor Perspectives in Biology 2(12):a003848, Cold Spring Harbor Laboratory Press, United States (Dec. 2010).

Dong, H., et al., "Tumor-associated B7-H1 Promotes T-cell Apoptosis: A Potential Mechanism of Immune Evasion," Nature Medicine 8(8):793-800, Nature Publishing Company, United States (Aug. 2002).

Gadiot, J., et al., "Overall Survival and PD-L1 Expression in Metastasized Malignant Melanoma," Cancer 117(10):2192-2201, American Cancer Society, United States (May 2011).

Garbe, C., et al., "Diagnosis and Treatment of Melanoma. European Consensus-based Interdisciplinary Guideline—Update 2012," European Journal of Cancer 48(15):2375-2390, Elsevier Ltd., England (Oct. 2012).

GenBank, "cytotoxic T-lymphocyte-associated protein 4 [*Homo sapiens*]," Accession No. AAB59385.1, Nov. 1, 1994, accessed at https://www.ncbi.nlm.nih.gov/protein/AAB59385, accessed on Dec. 6, 2016, 3 pages.

GenBank, "Human hPD-1 (hPD-1) mRNA, complete cds," Accession No. U64863.1, Oct. 12, 2005, accessed at https://www.ncbi.nlm.nih.gov/nuccore/U64863, accessed on Dec. 6, 2016, 3 pages.

GenBank, "RecName: Full=Programmed cell death 1 ligand 1; Short=PD-L1; Short=PDCD1 ligand 1; Short=Programmed death ligand 1; AltName: Full=B7 homolog 1; Short=B7-H1; AltName: CD_antigen=CD274; Flags: Precursor," Accession No. Q9NZQ7.1, Nov. 2, 2016, accessed at https://www.ncbi.nlm.nih.gov/protein/Q9NZQ7, accessed on Dec. 6, 2016, 11 pages.

Hamanishi, J., et al., "Programmed Cell Death 1 Ligand 1 and Tumor-infiltrating CD8+ T Lymphocytes are Prognostic Factors of

(56) References Cited

OTHER PUBLICATIONS

Human Ovarian Cancer," Proceedings of the National Academy of Sciences USA 104(9):3360-3365, National Academy of Sciences, United States (Feb. 2007).

Herbst, R.S., et al., "A Study of MPDL3280A, an Engineered PD-L1 Antibody in Patients with Locally Advanced or Metastatic Tumors," Journal of Clinical Oncology 31(Suppl; Abstr 3000), American Society of Clinical Oncology, United States (May 2013).

International Search Report and Written Opinion for International Application No. PCT/US2016/029877, European Patent Office, Rijswijk, mailed on Jul. 13, 2016, 16 pages.

Khleif, S., et al., "MEDI4736, An Anti-PD-L1 Antibody with Modified Fc Domain: Preclinical Evaluation and Early Clinical Results from a Phase 1 Study in Patients with Advanced Solid Tumors," Abstract 802, in Proceedings from the European Cancer Congress 2013, Amsterdam, The Netherlands (Sep. 27-Oct. 1, 2013).

Mahoney, K.M., et al., "The Next Immune-Checkpoint Inhibitors: PD-1/PD-L1 Blockade in Melanoma," Clinical Therapeutics 37(4):764-782, Elsevier HS Journals, Inc., United States (Mar. 2015).

Marzuka, A., et al., "Melanoma Treatments: Advances and Mechanisms," Journal of Cellular Physiology 230(11):2626-2633, Wiley Periodicals, Inc., United States (Jul. 2015).

McCabe, K.E. and Wu, A.M., "Positive Progress in ImmunoPET—Not Just a Coincidence," Cancer Biotherapy & Radiopharmaceuticals 25(3):253-261, Mary Ann Liebert, Inc., United States (Jun. 2010).

National Comprehensive Cancer Network, "NCCN Guidelines," nccn.org, accessed at http://www.nccn.org/professionals/physician_gls/f_guidelines.asp#site, accessed on Dec. 8, 2016, 4 pages.

NCI Drug Dictionary, anti-PD-1 Fusion Protein AMP-224, accessed on Dec. 1, 2016, retrieved from the Internet URL: https://www.cancer.gov/publications/dictionaries/cancer-drug?cdrid=700595.

NCI Drug Dictionary, anti-PD-1 monoclonal antibody MEDI0680, accessed on Dec. 1, 2016, retrieved from the Internet URL: https://www.cancer.gov/publications/dictionaries/cancer-drug?cdrid=756047.

NCI Drug Dictionary, pembrolizumab, accessed on Dec. 1, 2016, retrieved from the Internet URL: https://www.cancer.gov/drugdictionary?cancer-drug?cdrid=695789.

Olafsen, T., et al., "ImmunoPET imaging of B-Cell Lymphoma Using $^{124}$I-Anti-CD20 scFv Dimers (Diabodies)," Protein Engineering, Design & Selection 23(4):243-249, Oxford University Press, England (Apr. 2010).

Ott, P.A., et al., "CTLA-4 and PD-1/PD-L1 Blockade: New Immunotherapeutic Modalities with Durable Clinical Benefit in Melanoma Patients," Clinical Cancer Research 19(19):5300-5309, American Association of Cancer Research, United States (Oct. 2013).

Philips, G.K. and Atkins, M., "Therapeutic Uses of Anti-PD-1 and Anti-PD-L1 Antibodies," International Immunology 27(1):39-46, The Japanese Society for Immunology, Japan (Oct. 16, 2014).

Siegel, R., et al., "Cancer Statistics, 2013," CA: A Cancer Journal for Clinicians 63(1):11-30, American Cancer Society, United States (Jan. 2013).

Sjoblom, T., et al., "The Consensus Coding Sequences of Human Breast and Colorectal Cancers," Science 314(5797):268-274, American Association for the Advancement of Science, United States (Sep. 2006).

Taube, J.M., et al., "Colocalization of Inflammatory Response With B7-H1 Expression in Human Melanocytic Lesions Supports an Adaptive Resistance Mechanism of Immune Escape," Science Translational Medicine 4(127):127ra37, American Association for the Advancement of Science, United States (Mar. 2012).

Topalian, S.L., et al., "Safety, Activity, and Immune Correlates of Anti-PD-1 Antibody in Cancer," The New England Journal of Medicine 366(26):2443-2454, Massachusetts Medical Society, United States (Jun. 2012).

United States Adopted Name (USAN) Drug Finder, "Pembrolizumab: Statement on a nonproprietary name adopted by the USAN Council (ZZ-165)," published Nov. 27, 2013, accessed at https://searchusan.

ama-assn.org/usan/documentDownload?uri=%2Funstructured%2Fbinary%2Fusan%2Fpembrolizumab.pdf, accessed on Dec. 8, 2016, 2 pages.

Wang, C., et al., "In Vitro Characterization of the Anti-PD-1 Antibody Nivolumab, BMS-936558, and In Vivo Toxicology in Non-Human Primates," Cancer Immunology Research 2(9):846-856, American Association for Cancer Research, United States (May 2014).

Wolchok, J.D., et al., "Nivolumab plus Ipilimumab in Advanced Melanoma," The New England Journal of Medicine 369(2):122-133, Massachusetts Medical Society, United States (Jul. 2013).

International Search Report and Written Opinion for International Application No. PCT/US2016/029878, European Patent Office, Rijswijk, mailed on Jul. 13, 2016, 15 pages.

Office Action mailed Feb. 28, 2018, in U.S. Appl. No. 15/141,769, Yang, A., et al., filed Apr. 28, 2016, 12 pages.

Office Action mailed Jun. 22, 2018, in U.S. Appl. No. 15/141,769, Yang, A., et al., filed Apr. 28, 2016, 7 pages.

Kuenen, B., et al. "A Phase I Pharmacologic Study of Necitumumab (IMC-11 F8), a Fully Human IgG1 Monoclonal Antibody Directed Against EGFR in Patients with Advanced Solid Malignancies," Clin Cancer Res. 16(6):1915-23, American Association for Cancer Research, United States (Mar. 2010).

Wang, D.D., et al. "Fixed Dosing Versus Body Size-Based Dosing of Monoclonal Antibodies in Adult Clinical Trials," J Clin Pharmacol. 49(9):1012-24, United States (Sep. 2009).

Office Action mailed May 2, 2018, in U.S. Appl. No. 15/311,409, Feltquate, D et al., filed Nov. 15, 2016, 13 pages.

Office Action mailed Jun. 13, 2018, in U.S. Appl. No. 15/210,612, Manekas, D. et al., filed Jul. 14, 2016, 16 pages.

Bai, S., et al., "A Guide to Rational Dosing of Monoclonal Antibodies," Clin Pharmacokinetics 51(2):119-135, Springer-Business, United States (Feb. 2012).

Guler, E., et al., "A review of the fixed douse use of new oral anticoagulants in obese patients: Is it really enough?," Anatol J Cardiol 15:1020-1029, Turkish Society of Cardiology, Turkey (Dec. 2015).

Pan, S-D., et al., "Weight-based dosing in medication use: what should we know?," Patient Preference and Adherence 10:549-560, Dove Medical Press, United Kingdom (Apr. 2016).

Opdivo (nivolumab) [package insert], 32 pages; Bristol-Myers Squibb: Approved by U.S. Food and Drug Administration, United States; (Aug. 2018).

Tzartos, S.J., et al., "Epitope Mapping by Antibody Competition. Methodology and Evaluation of the Validity of the Technique," Methods in Molecular Biology 66:55-66, Humana Press, United States (1996).

Long, G.V., et al. "Assessment of nivolumab exposure and clinical safety of 480 mg every 4 weeks flat-dosing schedule in patients with cancer," Annals of Oncology 29(11):2208-13, Elsevier, Netherlands (Nov. 2018).

Pollack, M.H., et al., "Safety of resuming anti-PD-1 in patients with immune-related adverse events (irAEs) during combined anti-CTLA-4 and anti-PD1 in metastatic melanoma," Annals of Oncology 29(1):250-55, Elsevier, Netherlands (Jan. 2018).

Zhao, X., et al., "Assessment of nivolumab benefit-risk profile of a 240-mg flat dose relative to a 3-mg/kg dosing regimen in patients with advanced tumors," Annals of Oncology: Official Journal of the European Society for Medical Oncology 28(8):2002-2008, Oxford Journals, United Kingdom (Aug. 2017).

Office Action mailed Dec. 6, 2017, in U.S. Appl. No. 15/141,772, Yang, A. et al., filed Apr. 28, 2016, 17 pages.

Office Action mailed Apr. 12, 2018, in U.S. Appl. No. 15/141,772, Yang, A. et al., filed Apr. 28, 2016, 13 pages.

NCCN Guidelines (2014), available at: http://www.nccn.org/professionals/physician_gls/f_guidelines.asp#site, last accessed May 30, 2014.

Advisory Action mailed Aug. 3, 2018, in U.S. Appl. No. 15/141,772, Yang, Arvin et al., filed Apr. 28, 2016, 3 pages.

Gettinger, S.N., et al., "Overall Survival and Long-Term Safety of Nivolumab (Anti-Programmed Death 1 Antibody, BMS-936558, ONO-4538) in Patients with Previously treated Advanced Non-

(56) References Cited

OTHER PUBLICATIONS

Small-Cell Lung Cancer," Journal of Clinical Oncology 33(18): 2004-2012, American Society of Clinical Oncology, United States (Jun. 2015).

Johnson, D. B., et al., "Immune Checkpoint Inhibitors in NSCLC," Current Treatment Option in Oncology 15(4):658-669, SpringerLink, United States (Dec. 2014).

Office Action mailed Oct. 3, 2018 in U.S. Appl. No. 15/141,772, Yang, A et al., filed Apr. 28, 2016, 17 pages.

Naing, A., et al., "Anti-PD-1 monoclonal antibody MEDI0680 in a phase I study of patients with advanced solid malignancies," Journal of Immunotherapy of Cancer 7:225, Society for Immunotherapy of Cancer (SITC), United States (Aug. 2019).

Food and Drug Administration Label, "Opdivo," 110 pages (2021).

Food and Drug Administration Label, "Opdivo," 27 pages (2015).

Food and Drug Administration Label, "Keytruda," 106 pages (2020).

Food and Drug Administration Label, "Libtayo," 17 pages (2020).

Motzer, R., et al., "Nivolumab for Metastatic Renal Cell Carcinoma: Results of a Randomized Phase II Trial," J Clin Oncol 33(13):1430-1437, American Society of Clinical Oncology, United States (May 2015).

Brahmer, J., et al., "Phase I study of single-agent anti-programmed death-1 (MDX-1106) in refractory solid tumors: safety, clinical activity, pharmacodynamics, and immunologic correlates," J Clin Oncol 28:3167-3175, American Society of Clinical Oncology, United States (Jul. 2010).

Hodi, F., et al., "Improved survival with ipilimumab in patients with metastatic melanoma," N Engl J Med 363:711-723, Massachusetts Medical Society, United States (Aug. 2010).

Non-Comparative, Multi-Cohort, Single Arm, Open-Label, Phase 2 Study of Nivolumab (BMS-936558) in classical Hodgkin Lymphoma (cHL) Subjects. Adisinsight: Trials, 6 pages, Jul. 10, 2014.

Office Action mailed Aug. 11, 2021, in U.S. Appl. No. 16/240,316, Yang, A., filed Jan. 4, 2019, 17 pages.

Office Action mailed Oct. 22, 2021, in U.S. Appl. No. 16/430,106, Yang, A., filed Jun. 3, 2019, 30 pages.

Office Action mailed May 27, 2021, in U.S. Appl. No. 16/430,106, Yang, A., filed Jun. 3, 2019, 29 pages.

Office Action mailed Feb. 7, 2022, in U.S. Appl. No. 16/430,106, Yang, A., filed Jun. 3, 2019, 4 pages.

Burd, E.M., "Human Papillomavirus and Cervical Cancer," Clinical Microbiology Reviews 16(1):1-17, American Society for Microbiology, United States (2003).

Tsai, K.K., et al., "PD-1 and PD-L1 antibodies for melanoma," Human Vaccines & Immunotherapeutics 10(11):3111-3116, Taylor & Francis, United Kingdom (Aug. 2014).

Weber, J.S., et al., "Nivolumab versus chemotherapy in patients with advanced melanoma who progressed after anti-CTLA-4 treatment (CheckMate 037): a randomised, controlled, open-label, phase 3 trial," Lancet Oncol 16(4):375-384, The Lancet, United Kingdom (Apr. 2015).

Scott, L.J., "Nivolumab: A Review in Advanced Melanoma," Drugs 75(12):1413-24, Springer, Germany (Aug. 2015).

Bristol Myers Squibb Press Release, "European Commission Approves Expanded Use of Opdivo® (nivolumab) to Include Previously Treated Metastatic Non-Squamous Non-Small Cell Lung Cancer," published Apr. 6, 2016, 4 pages.

Brahmer, J., et al., "Nivolumab versus Docetaxel in Advanced Squamous-Cell Non-Small-Cell Lung Cancer," The New England Journal of Medicine 373(2):123-135, Massachusetts Medical Society, United States (Jul. 2015).

European Medicines Agency EMA, "Assessment report Opdivo International non-proprietary name: Nivolumab" 78 pages (Sep. 2015).

Spranger, S., et al., "Rational combinations of immunotherapeutics that target discrete pathways," J Immunother Cancer 1:16, BMJ, United Kingdom (Sep. 2013).

Topalian, S.L., et al., "Anti-pd-1 (Bms-936558, Mdx-1106) in Patients With Advanced Solid Tumors: Clinical Activity, Safety, and a Potential Biomarker for Response," Journal of Clinical Oncology 30(18), 1 page, Meeting Abstract: 2012 ASCO Annual Meeting II, American Society of Clinical Oncology, United States (Jun. 2012).

Larkin, J., et al., "Combined Nivolumab and Ipilimumab or Monotherapy in Untreated Melanoma," N Engl J Med 373(1):23-34, Massachusetts Medical Society, United States (Jul. 2015).

Larkin, J., et al., "Combined Nivolumab and Ipilimumab or Monotherapy in Previously Untreated Melanoma," N Engl J Med 373(1):23-34, Massachusetts Medical Society, United States (Jul. 2015).

ClinicalTrials.gov, "An Open-Label Phase II Study of Nivolumab in Adult Participants With Progessive/ Recurrent Meningioma," NCT02648997, published Jan. 24, 2024, accessed at https:// clinicaltrials.gov/study/NCT02648997, 17 pages.

ClinicalTrials.gov, "Phase II Anti-PD1 Epigenetic Therapy Study in NSCLC. (NA_00084192)," NCT01928576, published May 3, 2024, accessed at https://clinicaltrials.gov/study/NCT01928576, 15 pages.

ClinicalTrials.gov, "Study of BMS-936558 (Nivolumab) Compared to Docetaxel in Previously Treated Metastatic Non-squamous NSCLC (CheckMate057)," NCT01673867, published Feb. 8, 2023, accessed at https://clinicaltrials.gov/study/NCT01673867, 14 pages.

ClinicalTrials.gov, "Study of BMS-936558 (Nivolumab) Compared to Docetaxel in Previously Treated Advanced or Metastatic Squamous Cell Non-small Cell Lung Cancer (NSCLC) (CheckMate 017)," NCT01642004, published Dec. 28, 2022, accessed at https:// clinicaltrials.gov/study/NCT01642004, 16 pages.

Byrum, S., et al., "A Quantitative Proteomic Analysis of FFPE Melanoma," J. Cutan Pathol 38(11):933-936, Wiley, United States (Nov. 2011).

Opdivo, Highlights of Prescribing Information, 34 pages, Bristol-Myers Squibb Company, United States (Sep. 2015).

ClinicalTrials.gov, "Phase 3 Study of Nivolumab or Nivolumab Plus Ipilimumab Versus Ipilimumab Alone in Previously Untreated Advanced Melanoma (CheckMate 067)," NCT01844505, published Jul. 3, 2024, accessed at https://clinicaltrials.gov/study/NCT01844505, 17 pages.

U.S. Department of Health and Human Services Food and Drug Administration Center for Drug Evaluation and Research, "Guidance for Industry Exposure-Response Relationships—Study Design, Data Analysis, and Regulatory Applications," 28 pages (Apr. 2003).

ClinicalTrials.gov, "A Study to Compare BMS-936558 to the Physician's Choice of Either Dacarbazine or Carboplatin and Paclitaxel in Advanced Melanoma Patients That Have Progressed Following Anti-CTLA-4 Therapy (CheckMate 037)," NCT01721746, published Apr. 19, 2022, accessed at https://clinicaltrials.gov/study/ NCT01721746, 17 pages.

ClinicalTrials.gov, "A Single-Arm, Open-Label, Multicenter Clinical Trial With Nivolumab (BMS-936558) for Subjects With Histologically Confirmed Stage III (Unresectable) or Stage IV Melanoma Progressing Post Prior Treatment Containing an Anti-CTLA4 Monoclonal Antibody (CheckMate 172)," NCT02156804, published Sep. 11, 2020, accessed at https://clinicaltrials.gov/study/NCT02156804, 9 pages.

ClinicalTrials.gov, "Anti-PD 1 Brain Collaboration for Patients With Melanoma Brain Metastases (ABC)," NCT02374242, published Mar. 19, 2024, accessed at https://clinicaltrials.gov/study/ NCT02374242, 18 pages.

ClinicalTrials.gov, "An Investigational Immuno-therapy Study to Assess the Safety, Tolerability and Effectiveness of Anti-LAG-3 With and Without Anti-PD-1 in the Treatment of Solid Tumors," NCT01968109, published Jun. 20, 2024, accessed at https:// clinicaltrials.gov/study/NCT01968109, 15 pages.

Flies, D.B., et al., "Blockade of the B7-H1/PD-1 pathway for cancer immunotherapy," Yale J Biol Med 84(4):409-421, PMC, United States (Dec. 2011).

Toutain, P., et al., "Plasma terminal half-life," J Vet Pharmacol Ther 27(6):427-439, Wiley, United States (Dec. 2004).

ClinicalTrials.gov, "Small Cell Lung Carcinoma Trial With Nivolumab and IpiliMUmab in LImited Disease (STIMULI)," Record History of NCT02046733, published Feb. 8, 2021, accessed at https:// clinicaltrials.gov/study/NCT02046733?tab=history&a=1&b= 6#StudyPageTop, 27 pages.

ClinicalTrials.gov, "A Dose Frequency Optimization, Trial of Nivolumab 240 mg Every 2 Weeks vs Nivolumab 480 mg Every 4 Weeks in

(56) References Cited

OTHER PUBLICATIONS

Subjects With Advanced or Metastatic Non-small Cell Lung Cancer Who Received Up to 12 Months of Nivolumab at 3 mg/kg or 240 mg Every 2 Weeks (CheckMate 384)," NCT02713867, published Feb. 14, 2023, accessed at https://clinicaltrials.gov/study/NCT02713867, 15 pages.

Grosso, J., et al., "Association of Tumor PD-L1 Expression and Immune Biomarkers With Clinical Activity in Patients (Pts) With Advanced Solid Tumors Treated With Nivolumab (anti-PD-1; BMS-936558; ONO-4538)," Journal of Clinical Oncology 31(Suppl 15):3016, 3 Pages, Meeting Abstract: 2013 ASCO Annual Meeting I, American Society of Clinical Oncology, United States (May 2013).

Patel, S.P., et al., "PD-L1 Expression as a Predictive Biomarker in Cancer Immunotherapy," Molecular Cancer Therapeutics 14(4):847-856, American Association for Cancer Research, United States (Apr. 2015).

Berking, C., "ASCO 2015—Neues aus der Dermato-Onkologie," Trillium Krebsmedizin, 24(4):214-217, American Society of Clinical Oncology, United States (Jan. 2015).

Helwick, C., et al., "CheckMate 067: Dual Checkpoint Blockade Proves Effective in Advanced Melanoma," published Jun. 10, 2015, accessed at https://ascopost.com/issues/june-10-2015/checkmate-067-dual-checkpoint-blockade-proves-effective-in-advanced-melanoma/, 5 pages.

Hughes, D., "Nivolumab Significantly Improves Outcomes in Advanced Melanoma," published May 31, 2015, Cancer Therapy Advisor, accessed at https://www.cancertherapyadvisor.com/news/nivolumab-significantly-improves-outcomes-in-advanced-melanoma/, 6 pages.

The ASCO Post, "ASCO 2015: Phase III Study Finds Nivolumab Improves Progression-Free Survival, Especially When Combined With Ipilimumab, in Advanced Melanoma," published May 31, 2015, accessed at https://ascopost.com/News/28604, 5 pages.

Prichard, J.W., "Overview of automated immunohistochemistry," Arch Pathol Lab Med 138(12):1578-1582, Allen Press, United States (Dec. 2014).

Barbee, M., et al., "Current Status and Future Directions of the Immune Checkpoint Inhibitors Ipilimumab, Pembrolizumab, and Nivolumab in Oncology," Ann Pharmacother 49(8):907-37, Sage, United States (Aug. 2015).

Belum, V.R., et al., "Characterisation and management of dermatologic adverse events to agents targeting the PD-1 receptor," Eur J Cancer 60:12-25, Elsevier, Netherlands (Jun. 2016).

Postow, M.A., et al., "Immune Checkpoint Blockade in Cancer Therapy," J Clin Oncol 33(17):1974-1982, American Society of Clinical Oncology, United States (Jun. 2015).

Topalian, S.L., et al., "Survival, Durable Tumor Remission, and Long-Term Safety in Patients With Advanced Melanoma Receiving Nivolumab," J Clin Oncol 32(10):1020-1030, American Society of Clinical Oncology, United States (Apr. 2014).

Bi, Y., et al., "Model-informed drug development approach supporting approval of the 4-week (Q4W) dosing schedule for nivolumab (Opdivo) across multiple indications: a regulatory perspective," Ann Oncol 30(4):644-651, Elsevier, Netherlands (Apr. 2019).

Zhao, X., et al., "Model-based evaluation of the efficacy and safety of nivolumab once every 4 weeks across multiple tumor types," Ann Oncol 31(2):302-309, Elsevier, Netherlands (Feb. 2020).

Meng, X., et al., "Predictive biomarkers in PD-1/PD-L1 checkpoint blockade immunotherapy," Cancer Treat Rev 41(10):868-76, Elsevier, Netherlands (Dec. 2015).

Postow, M., et al., "Nivolumab and ipilimumab versus ipilimumab in untreated melanoma," N Engl J Med 372(21):2006-2017, Massachusetts Medical Society, United States (May 2015).

Bristol Myers Squibb Press Release, "Bristol-Myers Squibb Receives Approval from the U.S. Food and Drug Administration for the Opdivo (nivolumab) + Yervoy(ipilimumab) Regimen in BRAF V600 Wild-Type Unresectable or Metastatic Melanoma," published Oct. 1, 2015, 5 pages.

Anonymous, "CheckMate 067: Nivolumab + Ipilimumab and Nivolumab Alone Superior to Ipilimumab Alone in Previously Untreated Advanced Melanoma," Clinical Care Option Oncology D24a, Independent Conference Highlights of the 2015 ASCO Annual Meeting, American Society of Clinical Oncology, United States (Jun. 2, 2015).

Anonymous, "DAKO Autostainer," User Guide, Document No. 0003106, DAKO, Agilent, United States (Mar. 1, 2007), 2 pages.

Anonymous, "Summary of Product Characteristics: Yervoy 5 mg/ml concentrate for solution for infusion," pp. 1-90 (Apr. 2016).

ClinicalTrials.gov, "A Dose Escalation and Cohort Expansion Study of Anti-CD27 (Varlilumab) and Anti-PD-1 (Nivolumab) in Advanced Refractory Solid Tumors," History of Changes for Study: NCT02335918, dated Apr. 15, 2016, accessed at https://clinicaltrials.gov/ct2/history/NCT02335918?A=1&B=17&C=merged#StudyPageTop, 16 pages.

ClinicalTrials.gov, "A Dose Frequency Optimization, Trial of Nivolumab 240 mg Every 2 Weeks vs Nivolumab 480 mg Every 4 Weeks in Subjects With Advanced or Metastatic Non-small Cell Lung Cancer Who Received 4 Months of Nivolumab at 3 mg/kg or 240 mg Every 2 Weeks (CheckMate 384)," NCT02713867, dated Apr. 26, 2016, accessed at https://clinicaltrials.gov/ct2/show/NCT02713867, 18 pages.

ClinicalTrials.gov, "A Dose Frequency Optimization, Trial of Nivolumab 240 mg Every 2 Weeks vs Nivolumab 480 mg Every 4 Weeks in Subjects With Advanced or Metastatic Non-small Cell Lung Cancer Who Received Up to 12 Months of Nivolumab at 3 mg/?kg or 240 mg Every 2 Weeks (CheckMate 384)," History of Changes for Study: NCT02713867, dated Apr. 26, 2016, accessed at https://clinicaltrials.gov/ct2/history/NCT02713867?A=6&B=6&C=merged#StudyPageTop, 35 pages.

ClinicalTrials.gov, "A Single-Arm, Open-Label, Multicenter Clinical Trial With Nivolumab (BMS-936558) for Subjects With Histologically Confirmed Stage III (Unresectable) or Stage IV Melanoma Progressing Post Prior Treatment Containing an Anti-CTLA4 Monoclonal Antibody (CheckMate 172)," NCT02156804, dated Jun. 5, 2014, accessed at https://clinicaltrials.gov/ct2/show/NCT02156804, 11 Pages.

ClinicalTrials.gov, "A Study to Compare BMS-936558 to the Physician's Choice of Either Dacarbazine or Carboplatin and Paclitaxel in Advanced Melanoma Patients That Have Progressed Following Anti-CTLA-4 Therapy (CheckMate 037)," NCT01721746, dated Nov. 6, 2012, accessed at https://clinicaltrials.gov/ct2/show/NCT01721746, 14 pages.

ClinicalTrials.gov, "Safety Study of Anti-LAG-3 With and Without Anti-PD-1 in the Treatment of Solid Tumors," History of Changes for Study: NCT01968109, dated Oct. 6, 2014, accessed at https://clinicaltrials.gov/ct2/history/NCT01968109?A=1&B=8&C=merged#StudyPageTop, 16 pages.

ClinicalTrials.gov, "A Study of Nivolumab in Adult Participants with Recurrent High-Grade Meningioma," NCT02648997, dated Mar. 7, 2016, accessed at https://clinicaltrials.gov/ct2/show/NCT02648997, 6 pages.

ClinicalTrials.gov, "Anti-PD 1 Brain Collaboration for Patients With Melanoma Brain Metastases (ABC)," NCT02374242, dated Feb. 27, 2015, accessed at https://clinicaltrials.gov/ct2/show/NCT02374242, 18 pages.

ClinicalTrials.gov, "Small Cell Lung Carcinoma Trial With Nivolumab and IpiliMUmab in Limited Disease (STIMULI)," History of Changes for Study: NCT02046733, dated Oct. 6, 2015, accessed at https://clinicaltrials.gov/ct2/history/NCT02046733?A=1&B=6&C=merged#StudyPageTop, 22 pages.

ClinicalTrials.gov, "Phase 3 Study of Nivolumab or Nivolumab Plus Ipilimumab Versus Ipilimumab Alone in Previously Untreated Advanced Melanoma (CheckMate 067)," NCT01844505, dated May 1, 2013, accessed at https://clinicaltrials.gov/ct2/show/NCT01844505, 14 pages.

ClinicalTrials.gov, "Phase II Anti-PD1 Epigenetic Priming Study in NSCLC. (NA 00084192)," NCT01928576, dated Aug. 26, 2013, accessed at https://clinicaltrials.gov/ct2/show/NCT01928576, 5 pages.

ClinicalTrials.gov, "Study of BMS-936558 (Nivolumab) Compared to Docetaxel in Previously Treated Advanced or Metastatic Squamous Cell Non-small Cell Lung Cancer (NSCLC) (CheckMate 017)," NCT01642004, dated Jul. 17, 2012, accessed at ClinicalTrials.gov/NCT01642004, 11 pages.

ClinicalTrials.gov, "Study of BMS-936558 (Nivolumab) Compared to Docetaxel in Previously Treated Metastatic Non-squamous NSCLC Checkmate057," NCT01673867, dated Aug. 28, 2012, accessed at

(56)           References Cited

OTHER PUBLICATIONS https://clinicaltrials.gov/ct2/history/NCT01673867?A=55&B=55 &C=merged#StudyPageTop, 29 pages.

ClinicalTrials.gov, "Study of Nivolumab (BMS-936558) Compared With Dacarbazine in Untreated, Unresectable, Metastatic Melanoma," NCT01721772, dated Jan. 27, 2016, accessed at https://clinicaltrials.gov/ct2/history/NCT01721772?V_42= View#StudyPageTop, 23 pages.

ClinicalTrials.gov, "Study of Nivolumab (BMS-936558) vs. Everolimus in Pre-Treated Advanced or Metastatic Clear-cell Renal Cell Carcinoma (CheckMate 025)," NCT01668784, dated Aug. 20, 2012, accessed at https://www.clinicaltrials.gov/ct2/show/NCT01668784, 10 pages.

ClinicalTrials.gov, "Phase 3 Study of Nivolumab or Nivolumab Plus Ipilimumab Versus Ipilimumab Alone in Previously Untreated Advanced Melanoma (CheckMate 067)," NCT01844505, first posted May 1, 2013, accessed at https://clinicaltrials.gov/ct2/show/NCT01844505, dated Oct. 11, 2022, 12 pages.

Center For Drug Evaluation And Research, "Clinical Pharmacology and Biopharmaceutics Review(s)," FDA's Drug Approval Package for Opdivo (nivolumab), pp. 1-58, Food and Drug Administration, United States (Jan. 2015).

Anonymous, "Opdivo (Nivolumab) Injection, for Intravenous use," Highlights of Prescribing Information, pp. 1-74 (Mar. 2018).

Wang, X., et al., "Characterization of Exposure-response (E-R) Relationship for Nivolumab in Subject With Advanced Melanoma Pro-Gressing Post Anti-CTLA4," Clinical Pharmacology & Therapeutics 97(11): S42-S43, Wiley-Blackwell, United States (Feb. 2015).

Mallardo, D., et al., "24 Nivolumab serum concentration in metastatic melanoma patients could be related to anti-tumor activity gene and outcome," J Immunother Cancer 9(Suppl 2):A27-A28, BMJ, United States (Nov. 2021).

Simeone, E., et al., "Correlation of nivolumab 480 mg Q4W with better survival than other nivolumab monotherapy schedule in metastatic melanoma patients," J Clin Oncol 38(Suppl 15):e22008, 3 pages, American Society of Clinical Oncology, United States (May 2020).

Antonia et al., Phase I/II Study of Nivolumab With or Without Ipilimumab for Treatment of Recurrent Small Cell Lung Cancer (SCLC): CA209-032., J Clin Oncology. May 20, 2015; 33(15S).

Ascierto et al., Clinical Experiences with Anti-CD137 and Anti-PD1 Therapeutic Antibodies. Semin Oncol. Oct. 2010; 37(5):508-16.

Barbee et al., Current Status and Future Directions of the Immune Checkpoint Inhibitors Ipilimumab, Pembrolizumab, and Nivolumab in Oncology. Annals of Pharmacotherapy. May 2015, 49(8):907-937.

Bi et al., Model-Informed Drug Development Approach Supporting Approval of the 4-Week (Q4W) Dosing Schedule for Nivolumab (Opdivo) Across Multiple Indications: A Regulatory Perspective. Ann Oncol. Apr. 1, 2019; 30(4):644-651.

Callahan et al., Peripheral and Tumor Immune Correlates in Patients with Advanced Melanoma Treated with Combination Nivolumab (Anti- PD-1, BMS-936558, ONO-4538) and Ipilimumab. 2013 ASCO Annual Meeting (May 20, 2013).

Callahan et al., At the Bedside: CTLA-4- and PD-1-Blocking Antibodies in Cancer Immunotherapy. J Leukoc Biol. Jul. 2013; 94(1): 41-53.

Curran et al., PD-1 and CTLA-4 combination blockade expands infiltrating T cells and reduces regulatory T and myeloid cells within B16 melanoma tumors. Proc Natl Acad Sci USA. Mar. 2, 2010; 107(9):4275-4280.

Feng et al., Model-based Clinical Pharmacology Profiling of Ipilimumab in Patients with Advanced Melanoma. Br J Clin Pharmacol. Jul. 2014; 78(1):106-17.

Hammers et al., Expanded Cohort Results from CheckMate 016: A Phase I Study of Nivolumab in Combination with Ipilimumab in Metastatic Renal Cell Carcinoma (mRCC). J Clin Oncol., 33:15_ suppl, May 20, 2015.

Korman et al., Activity of Anti-PD-1 in murine tumor models: Role of 'host' PD-L1 and synergistic effect of anti-PD-1 and anti-CTLA-4. J Immunology. Apr. 2007; 178(1_Supplement):S82 (abstract). DOI:10.4049/jimmunol.178.Supp.48.37.

Lipson et al., Durable Cancer Regression Off-Treatment and Effective Reinduction Therapy with an Anti-PD-1 Antibody. Clin Cancer Res. Jan. 15, 2013;19(2):462-8.

Lipson et al., Ipilimumab: An Anti-CTLA-4 Antibody. Clin Cancer Res. Nov. 15, 2011; 17(22):6958-62.

Mansh, M., Ipilimumab and Cancer Immunotherapy: A New Hope for Advanced Stage Melanoma. Yale J Biol Med. Dec. 2011; 84(4):381-389.

Mathijssen et al., Flat-Fixed Dosing Versus Body Surface Area-Based Dosing of Anticancer Drugs in Adults. Oncologist. Aug. 2007; 12(8):913-23.

Mould et al., Pharmacokinetics and Pharmacodynamics of Monoclonal Antibodies: Concepts and Lessons for Drug Development. BioDrugs. Feb. 1, 2010; 24(1):23-39.

NCT00094653 Version 1, Brief Title: "MDX-010 Antibody, MDX-1379 Melanoma Vaccine, or MDX-010/MDX-1379 Combination Treatment for Patients with Melanoma" (Last Update Posted to clinicaltrials.gov: Jun. 24, 2005).

NCT00441337 Version 1, Brief Title: "Safety and PK Study of MDX- 1106 in Patients With Selected Refractory or Relapsed Malignancies" (Last Update Posted to clinicaltrials.gov: Feb. 28, 2007).

NCT00729950 Version 1, Brief Title: "Study of MDX-010 in Subjects With Unresectable Stage III or Stage IV Malignant Melanoma" (Last Update Posted to clinicaltrials.gov: Aug. 8, 2008).

NCT00730639 Version 1, Brief Title: "A Phase 1b Study of MDX-1106 in Subjects With Advanced or Recurrent Malignancies" (Last Update Posted to clinicaltrials.gov: Aug. 8, 2008).

NCT01024231 Version 3, Brief Title: "Dose-escalation Study of Combination BMS-936558 (MDX-1106) and Ipilimumab in Subjects With Unresectable Stage III or Stage IV Malignant Melanoma" (Last Update Posted to clinicaltrials.gov: Jan. 5, 2010).

NCT01024231 Version 58, Brief Title: "Dose-escalation Study of Combination BMS-936558 (MDX-1106) and Ipilimumab in Subjects With Unresectable Stage III or Stage IV Malignant Melanoma" (Last Update Posted to clinicaltrials.gov: May 1, 2012).

NCT01968109 Version 1, Brief Title: "Safety Study of Anti-LAG-3 With and Without Anti-PD-1 in the Treatment of Solid Tumors" (Last Update Posted to clinicaltrials.gov: Oct. 23, 2013).

NCT02713867 Version 2, Brief Title: "A Dose Frequency Optimization, Trial of Nivolumab 240 mg Every 2 Weeks vs Nivolumab 480 mg Every 4 Weeks in Subjects With Advanced or Metastatic Non-small Cell Lung Cancer Who Received 4 Months of Nivolumab at 3 mg/ kg or 240 mg Every 2 Weeks" (Last Update Posted to clinicaltrials. gov: Mar. 22, 2016).

Pardoll D., The blockade of immune checkpoints in cancer immunotherapy. Nat Rev Cancer. Mar. 22, 2012; 12(4):252-64.

Raedler et al., Opdivo (Nivolumab): Second PD-1 Inhibitor Receives FDA Approval for Unresectable or Metastatic Melanoma. Am Health Drug Benefits. Mar. 2015; 8(Spec Feature): 180-3.

Simeone et al., Immunomodulating antibodies in the treatment of metastatic melanoma: The experience with anti-CTLA-4, anti-CD137, and anti-PD1. J Immunotoxicol. Jul.-Sep. 2012; 9(3):241-7.

Sznol et al., Safety and antitumor activity of biweekly MDX-1106 (Anti- PD-1 Bms- 936558/ONO4538) in patients with advanced refractory malignancies. J Clin Oncology. May 20, 2010; 28(15).

Wolchok, J.D., et al., "Ipilimumab monotherapy in patients with pretreated advanced melanoma: a randomised, double-blind, multicentre, phase 2, dose-ranging study," Lancet Oncol. Feb. 2010; 11(2):155-64.

Zalevsky et al., Enhanced Antibody Half-Life Improves in Vivo Activity. Nat Biotechnol. Feb. 2010; 28(2):157-9.

Zhao et al., Model-Based Evaluation of the Efficacy and Safety of Nivolumab Once Every 4 Weeks Across Multiple Tumor Types. Ann Oncol. Feb. 2020; 31(2):302-309.

Anonymous, "CheckMate 067: Nivolumab + Ipilimumab and Nivolumab Alone Superior to Ipilimumab in Previously Untreated Advanced Melanoma" Clinical Care Options Oncology Independent Conference Highlights of the 2015 ASCO Annual Meeting,

(56)          References Cited

OTHER PUBLICATIONS

May 29-Jun. 2, 2015, Slide Set, American Society of Clinical Oncology, United States (May-Jun. 2015), 10 pages.

Clinicaltrials.gov, "History of Changes for Study: NCT01721772 Study of BMS-936558 vs. Dacarbazine in Untreated, Unresectable or Metastatic Melanoma," NCT01721772, Version 1, dated Nov. 2, 2012, accessed at https://clinicaltrials.gov/ct2/history/NCT01721772?A=1&B=1&C-merged#StudyPageTop, accessed on Nov. 17, 2021, 12 pages.

Clinicaltrials.gov, "History of Changes for Study: NCT01844505 Phase 3 Study of Nivolumab or Nivolumab Plus Ipilimumab Versus Ipilimumab Alone in Previously Untreated Advanced Melanoma (CheckMate-067)," NCT01844505, Version 1, dated Apr. 30, 2013, accessed at https://clinicaltrials.gov/ct2/history/NCT01844505?A=1&B=1&C=merged#StudyPageTop, accessed on Nov. 17, 2021, 15 pages.

Clinicaltrials.gov, "History of Changes for Study: NCT01844505 Phase 3 Study of Nivolumab or Nivolumab Plus Ipilimumab Versus Ipilimumab Alone in Previously Untreated Advanced Melanoma (CheckMate 067)," NCT01844505, Version 36, dated Apr. 20, 2015, accessed at https://clinicaltrials.gov/ct2/history/NCT01844505?A=36&B=36&C-merged#StudyPageTop, accessed on Dec. 3, 2021, 14 pages.

Clinicaltrials.gov, "History of Changes for Study: NCT02713867 A Dose Frequency Optimization, Phase IIIB/IV Trial of Nivolumab 240 mg Every 2 Weeks vs Nivolumab 480 mg Every 4 Weeks in Subjects With Advanced or Metastatic Non-small Cell Lung Cancer Who Received 4 Months of Nivolumab at 3 mg/kg or 240 mg Every 2 Weeks (CheckMate 384)," NCT02713867, Version 1, dated Mar. 15, 2016, accessed at https://clinicaltrials.gov/ct2/history/NCT02713867?A=1&B=1&C-merged#StudyPageTop, accessed on Nov. 17, 2021, 11 pages.

Declaration of Prof. Robert Charles Frederick Leonard (MD), dated Nov. 23, 2021, Exhibit D19, filed in EP Application No. 16724512, 12 pages.

European Medicines Agency, "Assessment report OPDIVO International non-proprietary name: Nivolumab" EMA/682492/2015, Committee for Medicinal Products for Human Use, dated Sep. 24, 2015, 78 pages.

European Medicines Agency, "Assessment report OPDIVO International non-propriety name: nivolumab," EMA/CHMP/76688/2015, Committee for Medicinal Products for Human Use, dated Apr. 23, 2015, 130 pages.

* cited by examiner

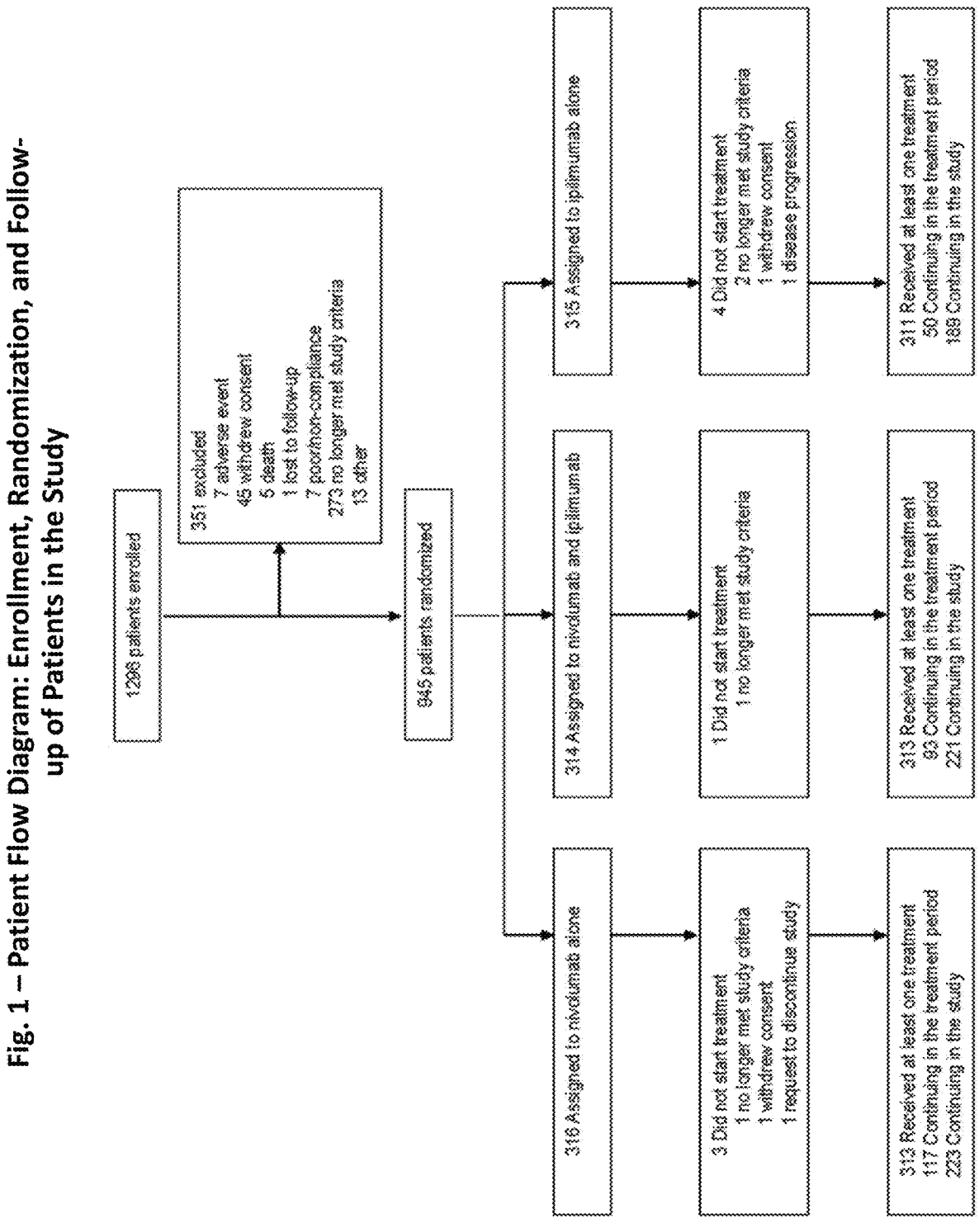
Fig. 1 – Patient Flow Diagram: Enrollment, Randomization, and Follow-up of Patients in the Study

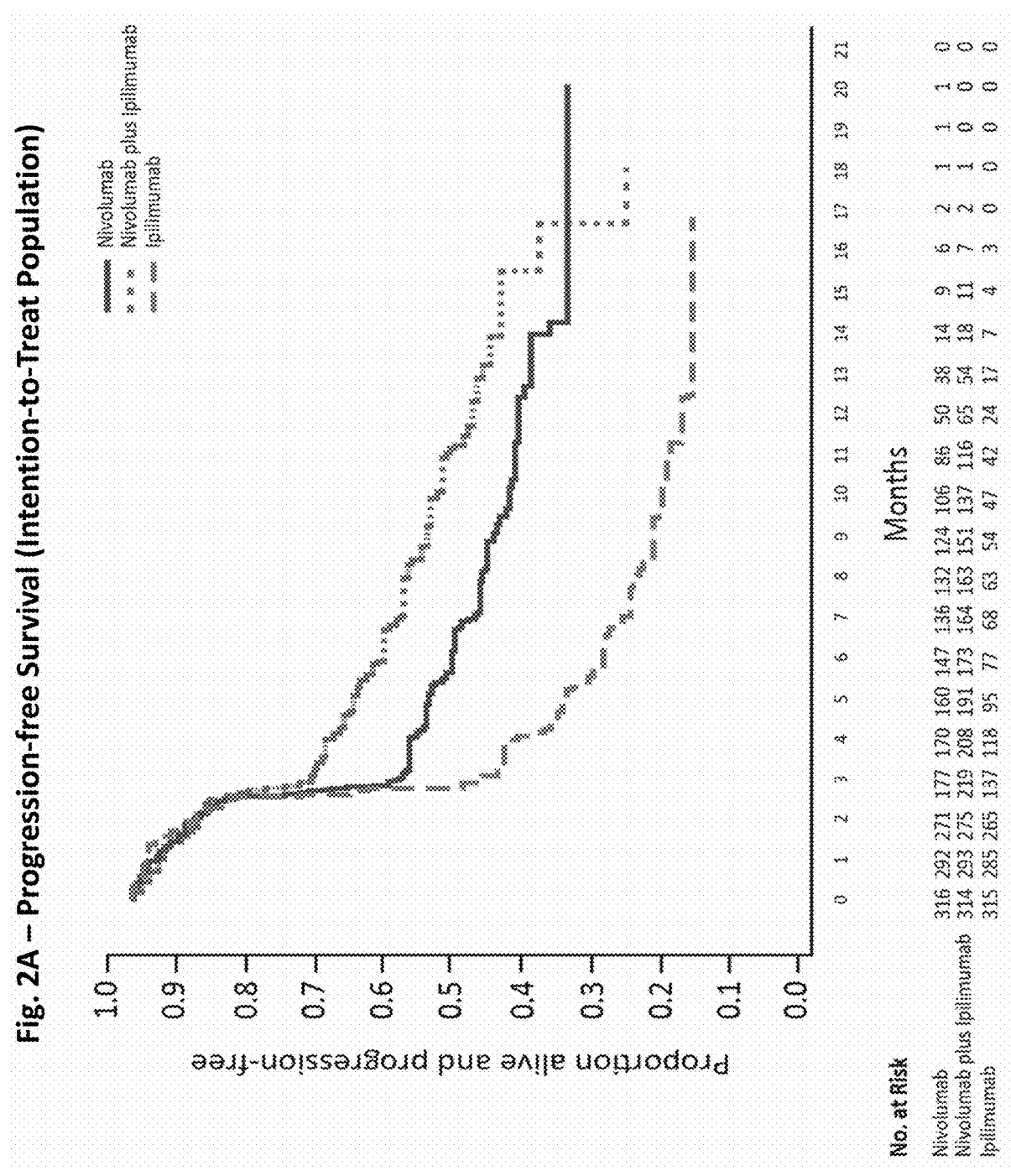
Fig. 2A – Progression-free Survival (Intention-to-Treat Population)

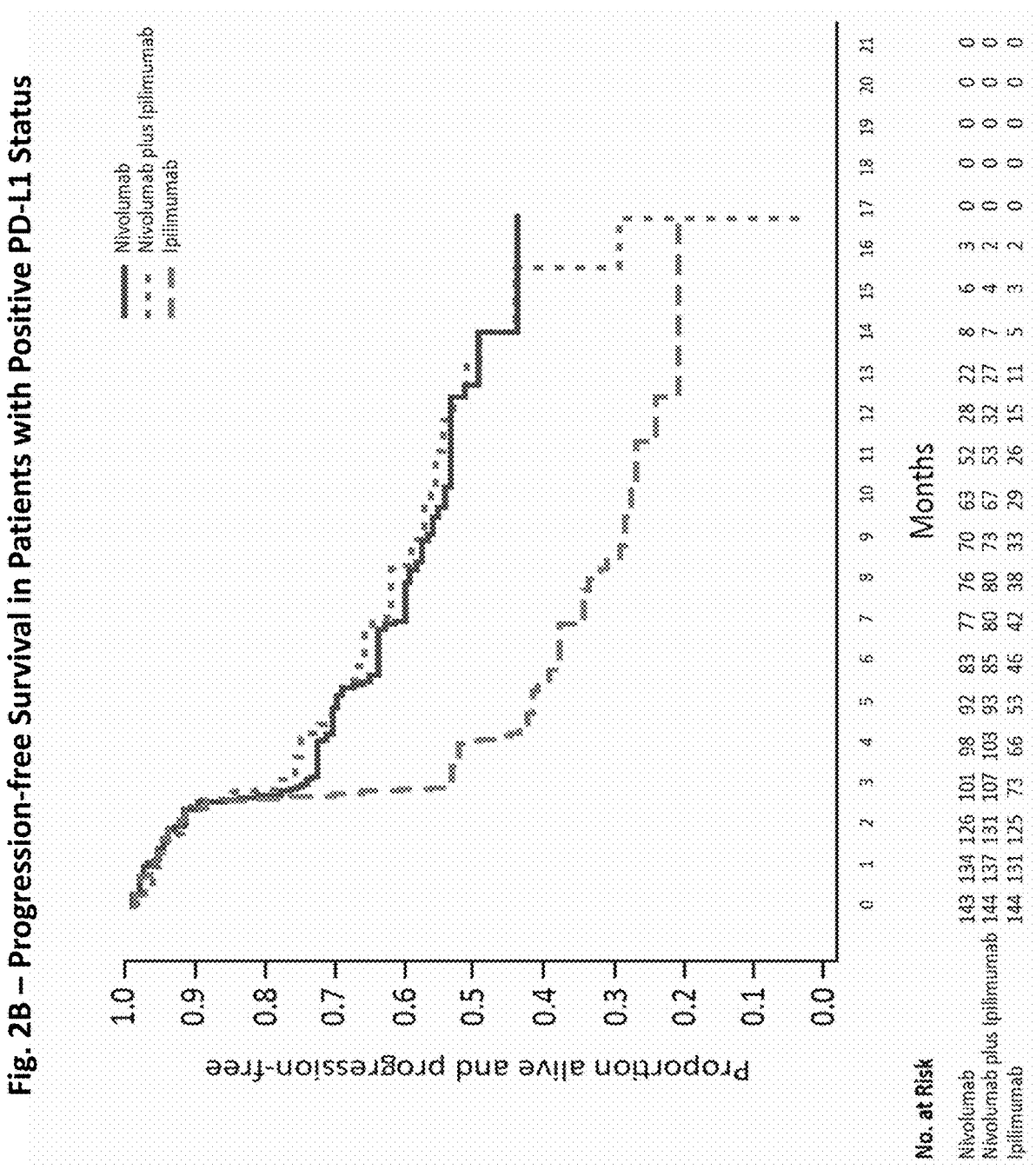
Fig. 2B – Progression-free Survival in Patients with Positive PD-L1 Status

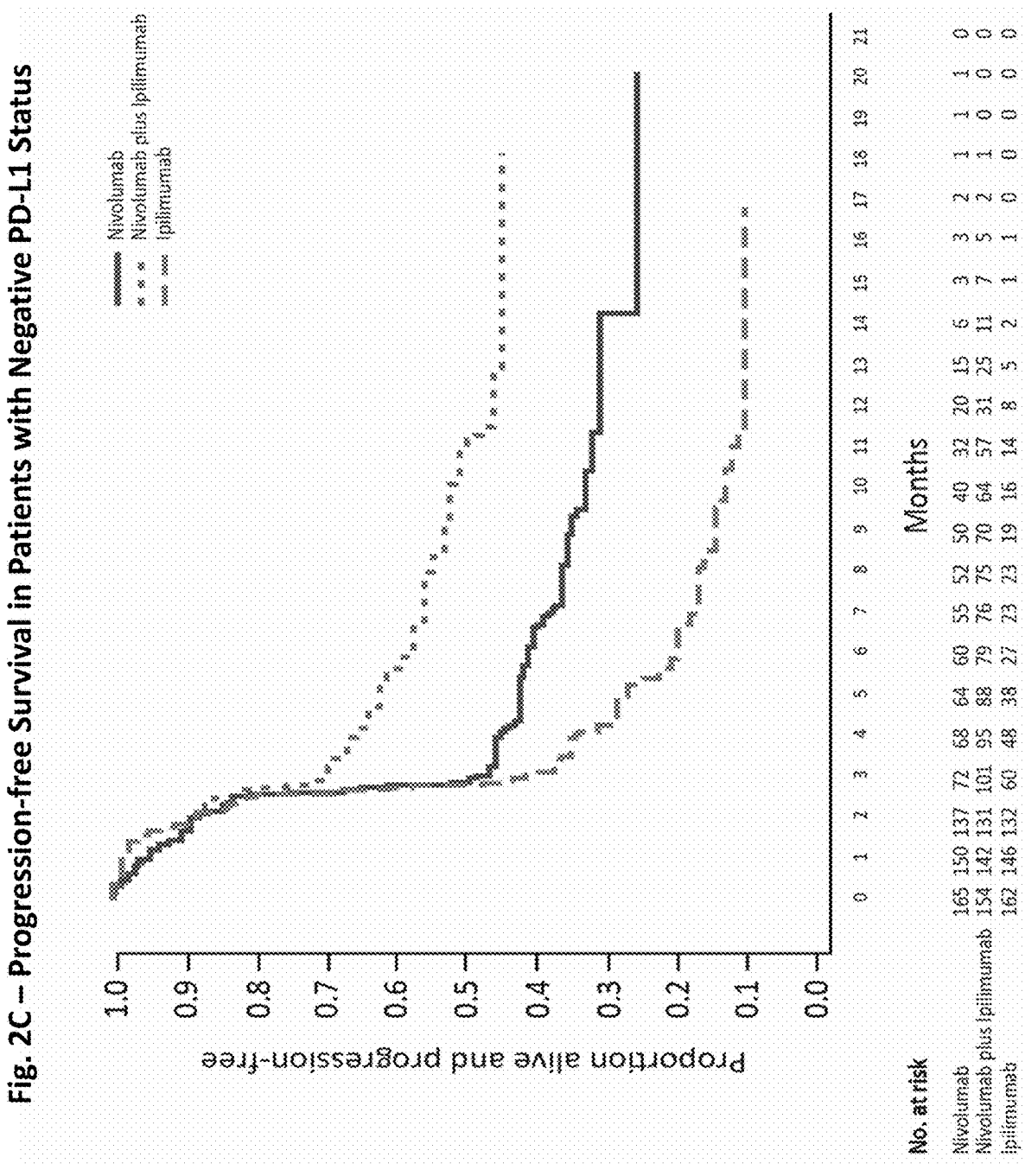
Fig. 2C — Progression-free Survival in Patients with Negative PD-L1 Status

Figures 3A, 3B:
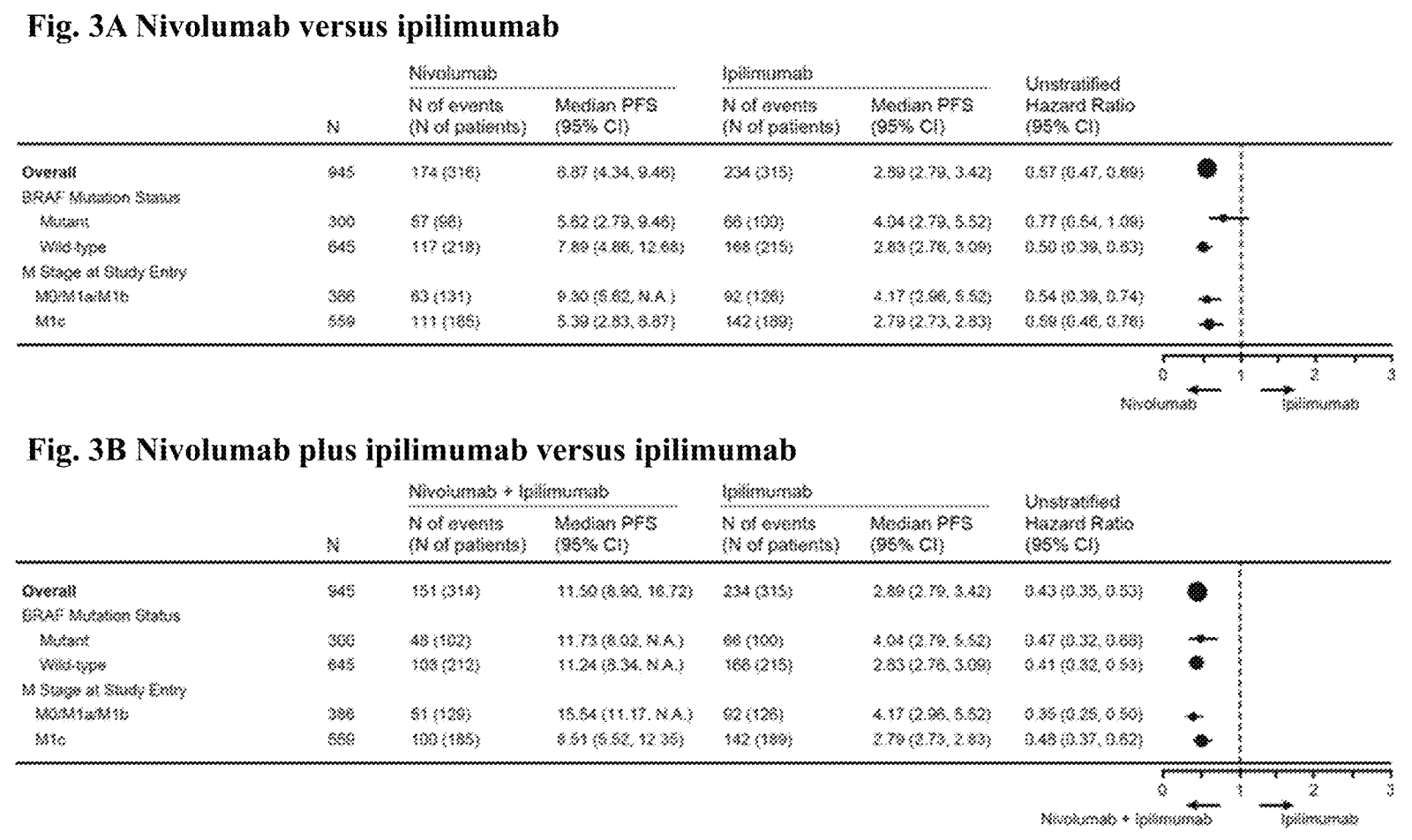

Fig. 3A Nivolumab versus ipilimumab

| | N | Nivolumab N of events (N of patients) | Median PFS (95% CI) | Ipilimumab N of events (N of patients) | Median PFS (95% CI) | Unstratified Hazard Ratio (95% CI) |
|---|---|---|---|---|---|---|
| Overall | 945 | 174 (316) | 6.87 (4.34, 9.40) | 234 (315) | 2.89 (2.79, 3.42) | 0.57 (0.47, 0.69) |
| BRAF Mutation Status | | | | | | |
| Mutant | 300 | 67 (98) | 8.82 (2.79, 9.46) | 86 (103) | 4.04 (2.79, 5.52) | 0.77 (0.54, 1.09) |
| Wild-type | 645 | 117 (218) | 7.69 (4.66, 12.68) | 168 (213) | 3.83 (2.76, 5.09) | 0.58 (0.39, 0.83) |
| M Stage at Study Entry | | | | | | |
| M0/M1a/M1b | 388 | 63 (131) | 9.60 (6.63, N.A.) | 92 (136) | 4.17 (3.66, 6.63) | 0.54 (0.39, 0.74) |
| M1c | 559 | 111 (185) | 5.39 (2.83, 6.97) | 142 (189) | 2.79 (2.73, 2.83) | 0.59 (0.46, 0.76) |

Fig. 3B Nivolumab plus ipilimumab versus ipilimumab

| | N | Nivolumab + ipilimumab N of events (N of patients) | Median PFS (95% CI) | Ipilimumab N of events (N of patients) | Median PFS (95% CI) | Unstratified Hazard Ratio (95% CI) |
|---|---|---|---|---|---|---|
| Overall | 945 | 151 (314) | 11.50 (8.90, 16.72) | 234 (315) | 2.89 (2.79, 3.42) | 0.43 (0.35, 0.53) |
| BRAF Mutation Status | | | | | | |
| Mutant | 300 | 49 (102) | 11.73 (8.02, N.A.) | 86 (103) | 4.04 (2.79, 5.52) | 0.47 (0.32, 0.68) |
| Wild-type | 645 | 106 (213) | 11.24 (8.34, N.A.) | 168 (213) | 2.83 (2.76, 5.09) | 0.41 (0.32, 0.54) |
| M Stage at Study Entry | | | | | | |
| M0/M1a/M1b | 388 | 51 (129) | 15.64 (11.17, N.A.) | 92 (136) | 4.17 (3.66, 6.63) | 0.35 (0.25, 0.50) |
| M1c | 559 | 100 (185) | 6.91 (5.52, 12.35) | 142 (189) | 2.79 (2.73, 2.83) | 0.48 (0.37, 0.62) |

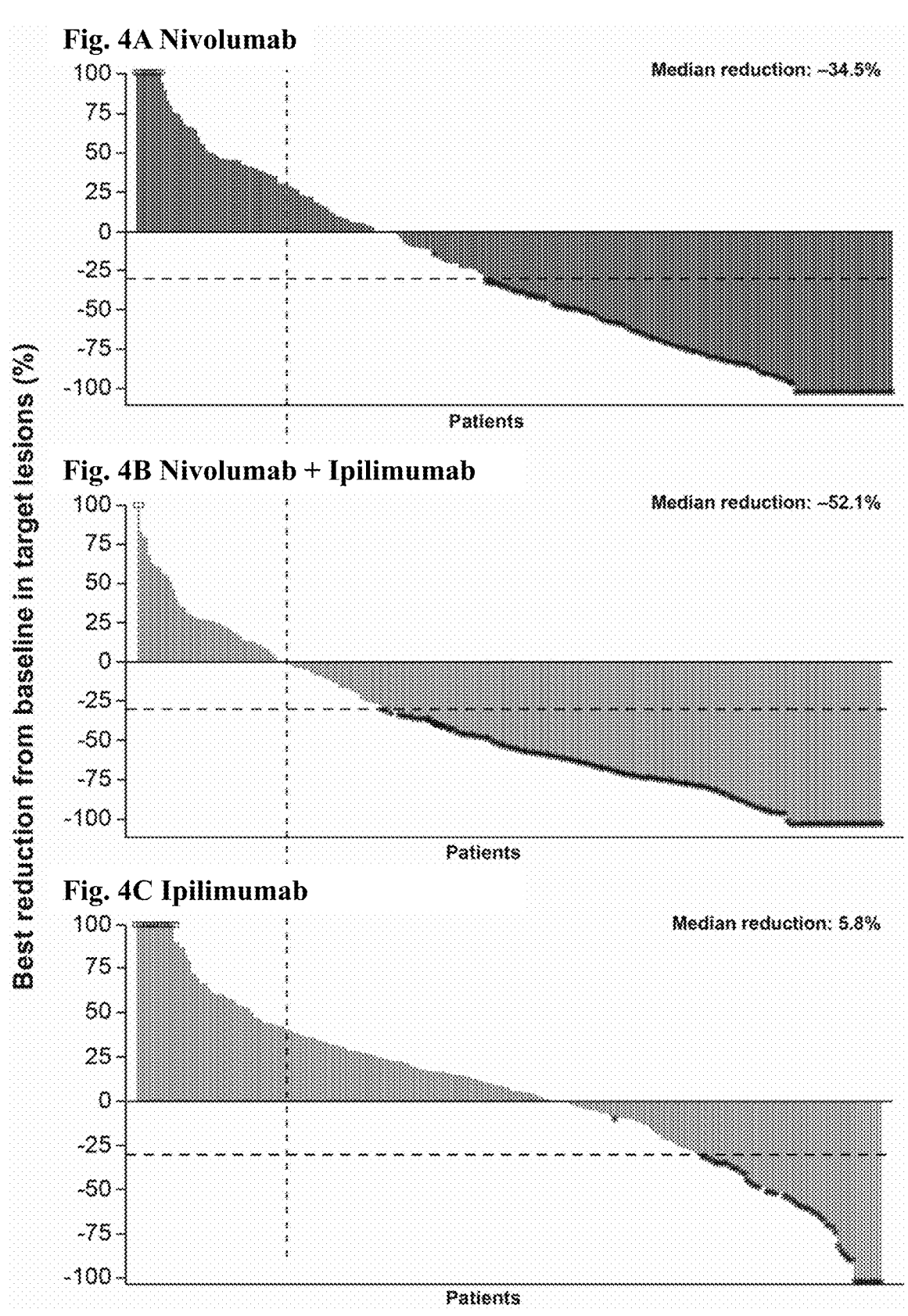
Fig. 4A Nivolumab
Median reduction: ~34.5%
Fig. 4B Nivolumab + Ipilimumab
Median reduction: ~52.1%
Fig. 4C Ipilimumab
Median reduction: 5.8%
Best reduction from baseline in target lesions (%)
Patients

1

TREATMENT OF PD-L1-POSITIVE MELANOMA USING AN ANTI-PD-1 ANTIBODY

CROSS-REFERENCE TO RELATED APPLICATIONS

The present application is a continuation of U.S. application Ser. No. 16/430,106 filed on Jun. 3, 2019, which is a continuation of U.S. application Ser. No. 15/141,772 filed Apr. 28, 2016, which claims benefit to U.S. Provisional Application No. 62/153,954 filed Apr. 28, 2015, each of which is incorporated herein by reference in its entirety.

REFERENCE TO A SEQUENCE LISTING SUBMITTED ELECTRONICALLY VIA EFS-WEB

The instant application contains a Sequence Listing which has been submitted in ASCII format via EFS-Web, and is hereby incorporated by reference in its entirety. Said ASCII copy, created on Mar. 22, 2022, is named 3338_0320004_Seqlisting_ST25.txt and is 3,785 bytes in size.

Throughout this application, various publications are referenced in parentheses by author name and date, or by patent No. or patent Publication No. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

FIELD OF THE INVENTION

This invention relates to a method of treating PD-L1-positive melanoma comprising administering an anti-PD-1 antibody.

BACKGROUND OF THE INVENTION

Human cancers harbor numerous genetic and epigenetic alterations, generating neoantigens potentially recognizable by the immune system (Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

Recently, several immune checkpoint pathway inhibitors have begun to provide new immunotherapeutic approaches for treating cancer, including the development of an antibody (Ab), ipilimumab (YERVOY®), that binds to and inhibits Cytotoxic T-Lymphocyte Antigen-4 (CTLA-4) for the treatment of patients with advanced melanoma and the development of antibodies such as nivolumab and pembrolizumab (formerly lambrolizumab; USAN Council Statement, (2013) Pembrolizumab: Statement on a nonproprietary name adopted by the USAN Council (ZZ-165), Nov. 27, 2013) that bind specifically to the Programmed Death-1 (PD-1) receptor and block the inhibitory PD-1/PD-1 ligand pathway.

The promise of the emerging field of personalized medicine is that advances in pharmacogenomics will increasingly be used to tailor therapeutics to defined sub-populations, and ultimately, individual patients in order to enhance efficacy and minimize adverse effects. Recent successes include, for example, the development of imatinib mesylate (GLEEVEC®), a protein tyrosine kinase inhibitor that inhibits the bcr-abl tyrosine kinase, to treat Philadelphia chromosome-positive chronic myelogenous leukemia (CML); crizotinib (XALKORI®) to treat the 5% of patients with late-stage non-small cell lung cancers who express a mutant anaplastic lymphoma kinase (ALK) gene; and vemurafenib (ZELBORAF®), an inhibitor of mutated B-RAF protein (V600E-BRAF) which is expressed in around half of melanoma tumors. However, unlike the clinical development of small molecule agents that target discrete activating mutations found in select cancer populations, a particular challenge in cancer immunotherapy has been the identification of mechanism-based predictive biomarkers to enable patient selection and guide on-treatment management.

SUMMARY OF THE INVENTION

The present disclosure provides a method for treating a melanoma comprising (i) identifying a patient having a PD-L1 positive melanoma tumor; and (ii) administering to the patient an anti-PD-1 antibody or an antigen-binding portion thereof that binds specifically to a human PD-1 ("anti-PD1 antibody monotherapy"), wherein the patient is not administered a combination of an anti-PD-1 antibody or an antigen-binding portion thereof and an anti-CTLA-4 antibody or an antigen-binding portion thereof that binds specifically to a human CTLA-4 ("combination therapy").

The present disclosure also provides a method for treating a melanoma comprising (i) identifying a patient having a PD-L1 positive melanoma tumor; (ii) administering to the patient an anti-PD-1 antibody monotherapy; and (iii) administering a combination therapy to the patient, wherein the patient does not show efficacy with the anti-PD-1 monotherapy.

The present disclosure further provides a method for treating a melanoma comprising administering to a patient afflicted with a melanoma tumor an anti-PD-1 antibody monotherapy, not a combination therapy, wherein the patient is identified as having a PD-L1 positive melanoma tumor prior to the administration.

The present disclosure also provides a method for extending a progression-free survival period for over 12 months in a patient afflicted with a melanoma tumor comprising administering to the patient an anti-PD-1 antibody monotherapy, wherein the patient is identified as having a melanoma tumor expressing PD-L1 prior to the administration and wherein the patient demonstrates progression-free survival for over 12 months. In some embodiments, the progression-free survival of the patient is extended after the administration for over about 13 months, about 14 months, about 15 months, about 16 months, about 17 months, about 18 months, about 2 years, about 3 years, about 4 years, about 5 years, about 6 years, about 7 years, about 8 years, about 9 years, or about 10 years. In one particular embodiment, the progression-free survival of the patient is extended for over 14 months.

The present disclosure also provides a method for reducing a tumor size at least by 10% in a patient afflicted with a melanoma tumor comprising administering to the patient an anti-PD-1 antibody monotherapy, wherein the patient is identified as having a melanoma tumor expressing PD-L1 prior to the administration and wherein the administration reduces the tumor size at least about 10%, about 20%, about 30%, about 40%, or about 50% compared to the tumor size prior to the administration.

In certain embodiments, the present disclosure provides a method for selecting a patient suitable for an anti-PD-1 antibody monotherapy comprising (i) identifying a patient having a PD-L1 positive melanoma tumor; and (ii) instructing a healthcare provider to administer to the patient an anti-PD-1 antibody monotherapy.

In some embodiments, the methods disclosed herein further comprise measuring a PD-L1 expression on a melanoma tumor. In certain embodiments, the measuring comprises assessing the proportion of cells in the test tissue sample that express PD-L1 on the cell surface. In one particular embodiment, the presence of PD-L1 is determined using an automated IHC assay.

The present disclosure also provides a kit for treating a patient afflicted with a melanoma tumor, the kit comprising (a) a dosage ranging from 0.1 to 10 mg/kg body weight of an anti-PD-1 antibody or an antigen-binding portion thereof; and (b) instructions for using the anti-PD-1 antibody or the antigen-binding portion thereof in a method disclosed herein. In certain embodiments, the kit further comprises a dosage ranging from 0.1 to 10 mg/kg body weight of an anti-CTLA-4 antibody or an antigen-binding portion thereof.

BRIEF DESCRIPTION OF THE FIGURES

FIG. 1 shows a patient flow diagram of the randomized, double-blind, multicenter, phase 3 trial.

FIGS. 2A-C show progression-free survival data in the intention-to-treat population (FIG. 2A), in patients with positive PD-L1 status (FIG. 2B), and Negative PD-L1 Status (FIG. 2C). Each graph shows the progression free survival for patients treated with nivolumab alone (solid line), ipilimumab alone (dashed line), or the combination of nivolumab and ipilimumab (dotted line) in months (FIGS. 2A-C). The number at risk in months for each of nivolumab, nivolumab plus ipilimumab, and ipilimumab is shown below each x-axis (FIGS. 2A-C). PD-L1 expression status is based on verified PD-L1 assay data (FIGS. 2B-C).

FIGS. 3A and 3B show subgroup analyses of progression-free survival among patients treated with nivolumab alone compared to ipilimumab alone (FIG. 3A) and patients treated with nivolumab plus ipilimumab compared to ipilimumab alone (FIG. 3B).

FIGS. 4A-4C show the tumor burden change in target lesions in patients treated with nivolumab alone (FIG. 4A), nivolumab plus ipilimumab (FIG. 4B), and ipilimumab alone (FIG. 4C). In each graph, the y-axis shows the best reduction from baseline in target lesions (%) and the x-axis represents each patient (FIGS. 4A-C).

DETAILED DESCRIPTION OF THE INVENTION

The present invention relates to identifying an optimal strategy for treating a PD-L1-positive melanoma. In particular, the present invention shows that for a PD-L1-positive melanoma, a monotherapy of an anti-PD-1 antibody or an antigen-binding portion thereof is a better option than a combination therapy of an anti-PD-1 antibody or an antigen-binding portion thereof and an anti-CTLA-4 antibody or an antigen-binding portion thereof. If the monotherapy of an anti-PD-L1 antibody does not work in the patient, however, a combination therapy of an anti-PD-1 antibody and an anti-CTLA-4 antibody can be used to treat the patient.

Definitions

In order that the present disclosure may be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of a composition comprising a therapeutic agent to a subject, using any of the various methods and delivery systems known to those skilled in the art. Routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, in some embodiments, orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, or disease associated with the use of a medical treatment. For example, an adverse event may be associated with activation of the immune system or expansion of immune system cells (e.g., T cells) in response to a treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region is comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A mAb is an example of an isolated antibody. MAbs may be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region is also derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "anti-antigen" antibody refers to an antibody that binds specifically to the antigen. For example, an anti-PD-1 antibody binds specifically to PD-1 and an anti-CTLA-4 antibody binds specifically to CTLA-4.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor.

"Cytotoxic T-Lymphocyte Antigen-4" (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

The term "progression-free survival," which can be abbreviated as PFS, as used herein refers to the length of time during and after the treatment of a solid tumor (i.e., melanoma) that a patient lives with the disease but it does not get worse.

"Dosing interval," as used herein, means the amount of time that elapses between multiple doses of a formulation disclosed herein being administered to a subject. Dosing interval can thus be indicated as ranges.

The term "dosing frequency" as used herein refers to the frequency of administering doses of a formulation disclosed herein in a given time. Dosing frequency can be indicated as the number of doses per a given time, e.g., once a week or once in two weeks.

The use of the term "fixed dose" with regard to a composition of the invention means that two or more different antibodies in a single composition are present in the composition in particular (fixed) ratios with each other. In some embodiments, the fixed dose is based on the weight (e.g., mg) of the antibodies. In certain embodiments, the fixed dose is based on the concentration (e.g., mg/ml) of the antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody to mg second antibody. For example, the 3:1 ratio of a first antibody and a second antibody can mean that a vial can contain about 240 mg of the first antibody and 80 mg of the second antibody or about 3 mg/ml of the first antibody and 1 mg/ml of the second antibody.

The use of the term "flat dose" with regard to the composition of the invention means a dose that is administered to a patient without regard for the weight or body surface area (BSA) of the patient. The flat dose is therefore not provided as a mg/kg dose, but rather as an absolute amount of the agent (e.g., the anti-CTLA-4 antibody and/or anti-PD-1 antibody). For example, a 60 kg person and a 100 kg person would receive the same dose of the composition (e.g., 240 mg of an anti-PD-1 antibody and 80 mg of an anti-CTLA-4 antibody in a single fixed dosing formulation vial containing both 240 mg of an anti-PD-1 antibody and 80 mg of an anti-CTLA-4 antibody (or two fixed dosing formulation vials containing 120 mg of an anti-PD-1 antibody and 40 mg of an anti-CTLA-4 antibody, etc.)).

The term "weight based dose" as referred to herein means that a dose that is administered to a patient is calculated based on the weight of the patient. For example, when a patient with 60 kg body weight requires 3 mg/kg of an anti-PD-1 antibody in combination with 1 mg/kg of an anti-CTLA-4 antibody, one can draw the appropriate amounts of the anti-PD-1 antibody (i.e., 180 mg) and the anti-CTLA-4 antibody (i.e., 60 mg) at once from a 3:1 ratio fixed dosing formulation of an anti-PD1 antibody and an anti-CTLA-4 antibody.

The term "single antibody composition" as used herein refers to a composition comprising antibodies that specifically bind to a single target, e.g., PD-1. As used herein, the single antibody composition can include a mixture of antibodies if the antibodies specifically bind to the same target, e.g., nivolumab and pembrolizumab. In other embodiments, a single antibody composition can include only one specific antibodies, e.g., nivolumab alone or pembrolizumab alone, but not a mixture thereof.

The term "anti-PD-1 antibody monotherapy" as used herein includes a therapy of an anti-PD-1 antibody without an anti-CTLA-4 antibody therapy. The anti-PD-1 antibody monotherapy comprises, consists essentially of, or consists of administering one or more doses of an anti-PD-1 antibody to a patient in need thereof, but does not include administering an anti-CTLA-4 antibody. In one embodiment, the anti-PD-1 antibody monotherapy comprises administering one or more doses of an anti-PD-1 antibody to a patient in need thereof, but does not include administering an anti-CTLA-4 antibody. In another embodiment, the anti-PD-1 antibody monotherapy comprises administering one or more doses of an anti-PD-1 antibody to a patient in need thereof, but does not include administering an antibody specifically targeting a protein other than PD-1. In other embodiments, the anti-PD-1 antibody monotherapy comprises administering one or more doses of an anti-PD-1 antibody to a patient in need thereof, but does not include administering another anti-cancer agent.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including antibodies, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "PD-L1 positive" or "PD-L1 expression positive," relating to cell surface PD-L1 expression, refers to the proportion of cells in a test tissue sample comprising tumor cells and tumor-infiltrating inflammatory cells above which the sample is scored as expressing cell surface PD-L1. For cell surface expression assayed by immunohistochemistry (IHC), e.g., with the mAb 28-8, the PD-L1 positive tumor or PD-L1 expression positive tumor means that at least about 0.01%, at least about 0.5%, at least about 1%, at least about 2%, at least about 3%, at least about 4%, at least aout 5%, at least about 6%, at least about 7%, at least about 8%, at least about 9%, at least about 10%, at least about 15%, at least about 20%, at least about 25%, or at least about 30% of the total number of cells express PD-L1. PD-L1 positive tumor or PD-L1 expression positive tumor can also be expressed herein as tumor expressing PD-L1. In other embodiments, the PD-L1 positive tumor or PD-L1 expression positive tumor means that at least about 0.1% to at least about 20% of the total number of cells express PD-L1. In certain embodiments, the PD-L1 positive tumor or PD-L1 expression positive tumor means that at least about 0.1% to at least about 10% of the total number of cells express PD-L1. In some embodiments, the PD-L1 positive or PD-L1 expression positive tumor means that at least about 1% of the total number of cells express PD-L1 on the cell surface. In other embodiments, the PD-L1 positive or PD-L1 expression positive tumor means that at least about 5% of the total number of cells express PD-L1 on the cell surface. In one particular embodiment, PD-L1 positive or PD-L1 expression positive tumor means that at least about 1%, or in the range of 1-5% of the total number of cells express PD-L1 on the cell surface.

"PD-L1 negative" or "PD-L1 expression negative," relating to cell surface PD-L1 expression, refers to the lack of a detectable amount of cell surface PD-L1. For cell surface expression assayed by IHC, e.g., with the mAb 28-8, a PD-L1 negative tumor or PD-L1 expression negative tumor means that less than 0.01% of cells express a detectable level of PD-L1. In some embodiments, a PD-L1 negative tumor or PD-L1 expression negative tumor means that zero (0) cells express a detectable level of PD-L1. In some embodiments, a PD-L1 negative or a PD-L1 expression negative tumor is any tumor other than a PD-L1 positive or a PD-L1 expression positive tumor.

"Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

"Programmed Death Ligand-1 (PD-L1)" is one of two cell surface glycoprotein ligands for PD-1 (the other being PD-L2) that down-regulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

A "patient" as used herein includes any patient who is afflicted with a cancer (e.g., melanoma). The terms "subject" and "patient" are used interchangeably herein.

A "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

"Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

A "tumor-infiltrating inflammatory cell" is any type of cell that typically participates in an inflammatory response in a subject and which infiltrates tumor tissue. Such cells include tumor-infiltrating lymphocytes (TILs), macrophages, monocytes, eosinophils, histiocytes and dendritic cells.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

The terms "about once a week," "once about every week," "once about every two weeks," or any other similar dosing interval terms as used herein means approximate number, and "about once a week" or "once about every week" can include every seven days±two days, i.e., every five days to every nine days. The dosing frequency of "once a week" thus can be every five days, every six days, every seven days, every eight days, or every nine days. "Once about every two weeks" can include every fourteen days±three days, i.e., every eleven days to every seventeen days. Similar approximations apply, for example, to once about every three weeks, once about every four weeks, once about every five weeks, once about every six weeks and once about every twelve weeks. In some embodiments, a dosing interval of once about every six weeks or once about every twelve weeks means that the first dose can be administered any day in the first week, and then the next dose can be administered any day in the sixth or twelfth week, respectively. In other embodiments, a dosing interval of once about every six weeks or once about every twelve weeks means that the first dose is administered on a particular day of the first week (e.g., Monday) and then the next dose is administered on the same day of the sixth or twelfth weeks (i.e., Monday), respectively.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

Methods of the Invention

The present invention is directed to a method for treating a PD-L1-positive melanoma in a subject in need thereof. In the general melanoma population (mix of PD-L1-negative tumors and PD-L1-positive tumors), a combination therapy of an anti-PD-L1 antibody and an anti-CTLA-4 antibody appears to provide better progression-free survival than a monotherapy of either an anti-PD-1 antibody or an anti-CTLA-4 antibody. See FIG. 2A. However, the present invention identifies that in a PD-L1-positive melanoma population, the progression-free survival of an anti-PD-1 antibody monotherapy is substantially the same as a combination therapy of an anti-PD-1 antibody and an anti-CTLA-4 antibody. See FIG. 2B. Therefore, in patients having a PD-L1-positive tumor, a monotherapy of an anti-PD-1 antibody can be as effective as a combination therapy. In order to reduce the toxicity of the combination therapy in the patient, the present invention provides identifying a patient having a PD-L1-positive tumor and providing a monotherapy of an anti-PD-1 antibody for the initial treatment option. The patient can be administered with a combination therapy of an anti-PD-1 antibody and an anti-CTLA-4 antibody if the initial option fails for any reasons.

In one embodiment, the invention includes a method of treating a melanoma comprising: (i) identifying a patient having a PD-L1-positive melanoma tumor; and (ii) administering to the patient a single antibody composition comprising an anti-PD-1 antibody or an antigen-binding portion thereof that binds specifically to a human PD-1, wherein the patient is not administered with a combination of an anti-PD-1 antibody or an antigen-binding portion thereof and an anti-CTLA-4 antibody or an antigen-binding portion thereof that binds specifically to a human CTLA-4 ("combination therapy"). The invention can also include a method for treating a melanoma comprising: (i) identifying a patient having a PD-L1-positive melanoma tumor; (ii) administering to the patient an anti-PD-1 antibody monotherapy; and (iii) administering a combination therapy, wherein the patient does not show efficacy with the anti-PD-1 antibody monotherapy.

In another embodiment, the invention includes a method for treating a melanoma comprising: (i) identifying a patient having a PD-L1 positive melanoma tumor; and (ii) administering to the patient: (a) an anti-PD-1 antibody or an antigen-binding portion thereof that binds specifically to a human PD-1 ("anti-PD1 antibody monotherapy"); or (b) a combination of an anti-PD-1 antibody or an antigen-binding portion thereof that binds specifically to a human PD-1 and an anti-CTLA-4 antibody or an antigen-binding portion thereof that binds specifically to a human CTLA-4 ("combination therapy"). Selection of either an anti-PD-1 antibody monotherapy or a combination therapy can be based on the patient's prior toxicity profile or prior history with either the monotherapy or the combination therapy.

In another embodiment, the invention includes a method for treating a melanoma comprising administering to a patient afflicted with a melanoma tumor an anti-PD1 antibody monotherapy, not a combination therapy, wherein the patient is identified as having a PD-L1-positive melanoma tumor prior to the administration. The methods of the present invention can further include (i) identifying a patient who does not show efficacy with the anti-PD-1 monotherapy; and (ii) administering a combination therapy to the patient who does not show efficacy with the anti-PD-1 monotherapy. In one particular embodiment, the invention includes a method for treating a melanoma comprising: (i) identifying a patient having a PD-L1 positive melanoma tumor; (ii) administering to the patient an anti-PD-1 antibody monotherapy; (iii) identifying a patient that does not show efficacy with the anti-PD-1 monotherapy; and (iv) administering a combination therapy to the patient who does not show efficacy with the anti-PD-1 monotherapy.

In certain embodiments, the invention includes a method for extending a progression-free survival period for over 12 months in a patient afflicted with a melanoma tumor comprising administering to the patient a monotherapy of an anti-PD-1 antibody or an antigen-binding portion thereof that binds specifically to a human PD-1, wherein the patient is identified as having a PD-L1-positive melanoma tumor prior to the administration and wherein the patient demonstrates progression-free survival for over 12 months. In other embodiments, the invention provides a method for extending a progression-free survival period for over 12 months in a patient afflicted with a melanoma tumor comprising: (i) identifying a patient having a PD-L1-positive melanoma tumor; (ii) administering to the patient an anti-PD-1 monotherapy; and (iii) administering a combination therapy to the patient who does not show efficacy with the anti-PD-1 monotherapy, wherein the patient demonstrates progression-free survival for over 12 months. According to the invention, the progression-free survival of the patient can be extended, after the administration, for over about 13 months, about 14 months, about 15 months, about 16 months, about 17 months, about 18 months, about 2 years, about 3 years, about 4 years, about 5 years, about 6 years, about 7 years, about 8 years, about 9 years, or about 10 years. In a particular embodiment, the progression-free survival of the patient is extended for over 14 months.

In still other embodiments, the invention is directed to a method for reducing a tumor size at least by 10% in a patient afflicted with a melanoma tumor comprising administering to the patient a monotherapy of an anti-PD-1 antibody or an antigen-binding portion thereof that binds specifically to a human PD-1, wherein the patient is identified as having a PD-L1-positive melanoma tumor prior to the administration and wherein the administration reduces the tumor size at least about 10%, about 20%, about 30%, about 40%, or about 50% compared to the tumor size prior to the administration. In yet other embodiments, the method comprises (i) identifying a patient having a PD-L1-positive melanoma tumor; and (ii) administering to the patient an anti-PD-1 antibody monotherapy; and (iii) administering a combination therapy to the patient who does not show efficacy with the anti-PD-1 monotherapy, wherein the administration reduces the tumor size at least about 10%, about 20%, about 30%, about 40%, or about 50% compared to the tumor size prior to the administration. The tumor size, after the administration, can be reduced at least about 60%, 70%, 80%, 90% or 100%. The tumor can be completely eliminated from the patient's body after the administration.

The invention can also include a method of preventing a relapse and/or induce a remission to a patient comprising administering to the patient a monotherapy of an anti-PD-1 antibody or an antigen-binding portion thereof that binds specifically to a human PD-1, wherein the patient is identified as having a PD-L1-positive melanoma tumor prior to the administration. In some embodiments, the method of the invention comprises (i) identifying a patient having a PD-L1-positive melanoma tumor; (ii) administering to the patient an anti-PD-1 antibody or an antigen-binding portion thereof that binds specifically to a human PD-1 as a monotherapy, and not a combination of an anti-PD-1 antibody or an antigen-binding portion thereof and an anti-CTLA-4 antibody or an antigen-binding portion thereof.

In certain embodiments, the invention includes a method for increasing an objective response rate to be higher than 55% in a patient population, wherein each patient of the patient population is afflicted with a melanoma tumor, in a cancer treatment comprising administering to the patient a monotherapy of an anti-PD-1 antibody or an antigen-binding portion thereof that binds specifically to a human PD-1, wherein each patient is identified as having a PD-L1 positive melanoma tumor prior to the administration and wherein the objective response rate is higher than 55%, 60%, 65%, 70%, or 75%. The method can further comprise administering a combination therapy of an anti-PD-1 antibody or an antigen-binding portion thereof and an anti-CTLA-4 antibody or an antigen-binding portion thereof to those patients who do not show efficacy with the anti-PD-1 monotherapy. In a particular embodiment, the method further comprises identifying each patient as having a PD-L1-positive melanoma tumor prior to the administration. In other embodiments, each patient in the methods can further be characterized by (i) extended progression-free survival for over 12 months, (ii) tumor size reduction at least about 10%, about 20%, about 30%, about 40%, or about 50% compared to the tumor size prior to the administration, or (iii) both. In some embodiments, the patient population can be at least 100 patients having a PD-L1 positive melanoma tumor. In some embodiments, the patient population can be at least 200, 300, 400, 500, 600, 700, 800, 900, or 1000 patients having a PD-L1 positive melanoma tumor.

In further embodiments, the invention provides a method for selecting a patient suitable for an anti-PD-1 antibody monotherapy comprising: (i) identifying a patient having a PD-L1-positive melanoma tumor; and (ii) instructing a healthcare provider to administer to the patient a monotherapy of an anti-PD-1 antibody or an antigen-binding portion thereof that binds specifically to a human PD-1. The method can further comprise administering the anti-PD-1 antibody or an antigen-binding portion thereof to the patient.

The disclosure also provides a method for treatment of a subject afflicted with a melanoma, which method comprises: (a) selecting a patient who has a PD-L1-positive tumor, (b) further selecting a patient who is not suitable for the anti-PD-1 antibody monotherapy, and (c) administering a combination therapy of an anti-PD-1 antibody and an anti-CTLA-4 antibody or a standard-of-care therapeutic, e.g., an anti-CTLA-4 antibody monotherapy, to the selected patient. The further selection of a patient who is not suitable for the monotherapy can be patients who do not respond to the monotherapy or who have too much toxicity to the monotherapy. Those patients may show efficacy to the combination therapy because, not bound by any theory, the combination therapy may utilize a different mechanism of action. In addition, the patients may be able to tolerate the combination therapy, which may have a lower dose of one or both antibodies.

The methods of the invention as a result of the anti-PD-1 monotherapy and/or the combination therapy can treat the melanoma tumor, reduce the tumor size, prevent growth of the tumor, eliminate the tumor from the patient, prevent a relapse of a tumor, induce a remission in a patient, or any combination thereof. In certain embodiments, the anti-PD-1 monotherapy and/or the combination therapy induces a complete response. In other embodiments, the anti-PD-1 monotherapy and/or the combination therapy induces a partial response.

Melanoma

Melanoma (MEL) is a malignant tumor of melanocytes, the melanin-producing cells found predominantly in skin. Though less common than other skin cancers, it is the most dangerous of skin cancers if not diagnosed early and causes the majority (75%) of skin cancer deaths. The incidence of MEL is increasing worldwide in Caucasian populations, especially where peoples with low amounts of skin pigmentation receive excessive ultraviolet light exposure from the sun. In Europe, the incidence rate is <10-20 per 100,000 population; in the USA 20-30 per 100,000; and in Australia, where the highest incidence is observed, 50-60 per 100,000 (Garbe et al., *Eur. J. Cancer.* 48(15):2375-90 (2012)). MEL accounts for about 5% of all new cases of cancer in the United States (U.S.), and the incidence continues to rise by almost 3% per year. This translates to an estimated 76,690 new cases in the U.S. in 2013 with 9,480 associated deaths (Siegel et al., *CA Cancer J. Clin.* 63(1):11-30 (2013)).

For in situ (stage 0) or early-stage MEL (Stages I-II), surgical excision is the primary treatment. In general, the prognosis is excellent for patients with localized disease and tumors 1.0 mm or less in thickness, with 5-year survival rates of more than 90% (NCCN GUIDELINES®, 2013—Melanoma). Where surgical excision is not feasible for in situ melanoma due to comorbidity or cosmetically sensitive tumor location, topical imiquimod (INN) and radiotherapy are emerging as treatments, especially for lentigo maligna. Chemotherapeutic agents for treating MEL include dacarbazine, temozolomide and imatinib for melanoma with a c-KIT mutation, high-dose interleukin-2, and paclitaxel with or without carboplatin. However, these treatments have modest success, with response rates below 20% in first-line (1L) and second-line (2L) settings.

For patients with localized melanomas more than 1.0 mm in thickness, survival rates range from 50-90%. The likelihood of regional nodal involvement increases with increasing tumor thickness. With Stage III MEL (clinically positive nodes and/or in-transit disease), 5-year survival rates range from 20-70%. By far the most lethal is Stage IV MEL where long-term survival in patients with distant metastatic melanoma is less than 10% (NCCN GUIDELINES®, 2013—melanoma).

The types of melanoma that can be treated with the present methods include, but are not limited to, lentigo maligna, lentigo maligna melanoma, superficial spreading melanoma, acral lentiginous melanoma, nucosal melanoma, nodular melanoma, polypoid melanoma, desmoplastic melanoma, amelanotic melanoma, soft-tissue melanoma, melanoma with small nevus-like cells, melanoma with features of a Spitz nevus, or uveal melanoma. The stages of melanoma that can be treated with the present methods include, but are not limited to, (i) Stage I/II (invasive melanoma): T1a characterized by less than 1.0 mm primary tumor thickness, without ulceration, and mitosis $<1/mm^2$; T1b characterized by less than 1.0 mm primary tumor thickness, with ulceration or mitoses $\geq 1/mm^2$; T2a characterized by 1.01-2.0 mm primary tumor thickness, without ulceration; (ii) Stage II (high risk melanoma): T2b characterized by 1.01-2.0 mm primary tumor thickness, with ulceration; T3a characterized by 2.01-4.0 mm primary tumor thickness, without ulceration; T3b characterized by 2.01-4.0 mm primary tumor thickness, with ulceration; T4a characterized by greater than 4.0 mm primary tumor thickness, without ulceration; or T4b characterized by greater than 4.0 mm primary tumor thickness, with ulceration; (iii) Stage III (regional metastasis): N1 characterized by single positive lymph node; N2 characterized by two to three positive lymph nodes or regional skin/in-transit metastasis; or N3 characterized by four positive lymph nodes or one lymph node and regional skin/in-transit metastases; and (iv) Stage IV (distant metastasis): M1a characterized by distant skin metastasis, normal LDH; M1b characterized by Lung metastasis, normal LDH; or M1c characterized by other distant metastasis or any distant metastasis with elevated LDH. PD-L1-positive tumors that are treatable by the present methods can have PD-L1 expression on the surface of tumor cells or tumor infiltrating inflammatory cells.

Measurement of PD-L1 Expression

In certain embodiments, identifying a patient suitable for a PD-1 monotherapy for the present methods includes measuring or assessing a PD-L1 expression on the surface of the melanoma tumor cells or tumor infiltrating inflammatory cells. The phrases "tumors expressing PD-L1," "PD-L1 expressing tumor," "PD-L1 positive tumor," and "PD-L1 expression positive tumor" are used interchangeably herein. The meaning of the phrases is provided elsewhere herein. The methods of measuring or assessing the PD-L1 expression can be achieved by any methods applicable.

In order to assess the PD-L1 expression, in one embodiment, a test tissue sample is obtained from the patient who is in need of the therapy. In another embodiment, the assessment of PD-L1 expression can be achieved without obtaining a test tissue sample. In some embodiments, selecting a suitable patient includes (i) optionally providing a test tissue sample obtained from a patient with cancer of the tissue, the test tissue sample comprising tumor cells and/or tumor-infiltrating inflammatory cells; and (ii) assessing the proportion of cells in the test tissue sample that express PD-L1 on the surface of the cells based on an assessment that the proportion of cells in the test tissue sample that express PD-L1 on the cell surface is higher than a predetermined threshold level.

In any of the methods comprising the measurement of PD-L1 expression in a test tissue sample, however, it should be understood that the step comprising the provision of a test tissue sample obtained from a patient is an optional step. That is, in certain embodiments the method includes this step, and in other embodiments, this step is not included in the method. It should also be understood that in certain embodiments the "measuring" or "assessing" step to identify, or determine the number or proportion of, cells in the test tissue sample that express PD-L1 on the cell surface is performed by a transformative method of assaying for PD-L1 expression, for example by performing a reverse transcriptase-polymerase chain reaction (RT-PCR) assay or an IHC assay. In certain other embodiments, no transformative step is involved and PD-L1 expression is assessed by, for example, reviewing a report of test results from a laboratory. In certain embodiments, the steps of the methods up to, and including, assessing PD-L1 expression provides an intermediate result that may be provided to a physician or other healthcare provider for use in selecting a suitable candidate for the combination therapy of an anti-PD-1 antibody and an anti-CTLA-4 antibody. In certain embodiments, the steps that provide the intermediate result is performed by a medical practitioner or someone acting under the direction of a medical practitioner. In other embodiments, these steps are performed by an independent laboratory or by an independent person such as a laboratory technician.

In certain embodiments of any of the present methods, the proportion of cells that express PD-L1 is assessed by performing an assay to determine the presence of PD-L1 RNA. In further embodiments, the presence of PD-L1 RNA is determined by RT-PCR, in situ hybridization or RNase protection. In other embodiments, the proportion of cells that express PD-L1 is assessed by performing an assay to determine the presence of PD-L1 polypeptide. In further embodiments, the presence of PD-L1 polypeptide is determined by immunohistochemistry (IHC), enzyme-linked immunosorbent assay (ELISA), in vivo imaging, or flow cytometry. In some embodiments, PD-L1 expression is assayed by IHC. In other embodiments of all of these methods, cell surface expression of PD-L1 is assayed using, e.g., IHC or in vivo imaging.

Imaging techniques have provided important tools in cancer research and treatment. Recent developments in molecular imaging systems, including positron emission tomography (PET), single-photon emission computed tomography (SPECT), fluorescence reflectance imaging (FRI), fluorescence-mediated tomography (FMT), bioluminescence imaging (BLI), laser-scanning confocal microscopy (LSCM) and multiphoton microscopy (MPM), will likely herald even greater use of these techniques in cancer research. Some of these molecular imaging systems allow clinicians to not only see where a tumor is located in the body, but also to visualize the expression and activity of specific molecules, cells, and biological processes that influence tumor behavior and/or responsiveness to therapeutic drugs (Condeelis and Weissleder, *Cold Spring Harb. Per-*

*spect. Biol.* 2(12):a003848 (2010)). Antibody specificity, coupled with the sensitivity and resolution of PET, makes immunoPET imaging particularly attractive for monitoring and assaying expression of antigens in tissue samples (McCabe and Wu, *Cancer Biother. Radiopharm.* 25(3):253-61 (2010); Olafsen et al., *Protein Eng. Des. Sel.* 23(4):243-9 (2010)). In certain embodiments of any of the present methods, PD-L1 expression is assayed by immunoPET imaging. In certain embodiments of any of the present methods, the proportion of cells in a test tissue sample that express PD-L1 is assessed by performing an assay to determine the presence of PD-L1 polypeptide on the surface of cells in the test tissue sample. In certain embodiments, the test tissue sample is a FFPE tissue sample. In other embodiments, the presence of PD-L1 polypeptide is determined by IHC assay. In further embodiments, the IHC assay is performed using an automated process. In some embodiments, the IHC assay is performed using an anti-PD-L1 mAb to bind to the PD-L1 polypeptide.

Assaying Cell-Surface PD-L1 Expression by Automated IHC

In one embodiment of the present methods, an automated IHC method is used to assay the expression of PD-L1 on the surface of cells in FFPE tissue specimens. This disclosure provides methods for detecting the presence of human PD-L1 antigen in a test tissue sample, or quantifying the level of human PD-L1 antigen or the proportion of cells in the sample that express the antigen, which methods comprise contacting the test sample, and a negative control sample, with a mAb that specifically binds to human PD-L1, under conditions that allow for formation of a complex between the antibody or portion thereof and human PD-L1. In certain embodiments, the test and control tissue samples are FFPE samples. The formation of a complex is then detected, wherein a difference in complex formation between the test sample and the negative control sample is indicative of the presence of human PD-L1 antigen in the sample. Various methods are used to quantify PD-L1 expression.

In a particular embodiment, the automated IHC method comprises: (a) deparaffinizing and rehydrating mounted tissue sections in an autostainer; (b) retrieving antigen using a decloaking chamber and pH 6 buffer, heated to 110° C. for 10 min; (c) setting up reagents on an autostainer; and (d) running the autostainer to include steps of neutralizing endogenous peroxidase in the tissue specimen; blocking non-specific protein-binding sites on the slides; incubating the slides with primary Ab; incubating with a postprimary blocking agent; incubating with NovoLink Polymer; adding a chromogen substrate and developing; and counterstaining with hematoxylin.

For assessing PD-L1 expression in tumor tissue samples, a pathologist examines the number of membrane PD-L1$^+$ tumor cells in each field under a microscope and mentally estimates the percentage of cells that are positive, then averages them to come to the final percentage. The different staining intensities are defined as 0/negative, 1+/weak, 2+/moderate, and 3+/strong. Typically, percentage values are first assigned to the 0 and 3+ buckets, and then the intermediate 1+ and 2+ intensities are considered. For highly heterogeneous tissues, the specimen is divided into zones, and each zone is scored separately and then combined into a single set of percentage values. The percentages of negative and positive cells for the different staining intensities are determined from each area and a median value is given to each zone. A final percentage value is given to the tissue for each staining intensity category: negative, 1+, 2+, and 3+. The sum of all staining intensities needs to be 100%.

Staining is also assessed in tumor-infiltrating inflammatory cells such as macrophages and lymphocytes. In most cases macrophages serve as an internal positive control since staining is observed in a large proportion of macrophages. While not required to stain with 3+ intensity, an absence of staining of macrophages should be taken into account to rule out any technical failure. Macrophages and lymphocytes are assessed for plasma membrane staining and only recorded for all samples as being positive or negative for each cell category. Staining is also characterized according to an outside/inside tumor immune cell designation. "Inside" means the immune cell is within the tumor tissue and/or on the boundaries of the tumor region without being physically intercalated among the tumor cells. "Outside" means that there is no physical association with the tumor, the immune cells being found in the periphery associated with connective or any associated adjacent tissue.

In certain embodiments of these scoring methods, the samples are scored by two pathologists operating independently, and the scores are subsequently consolidated. In certain other embodiments, the identification of positive and negative cells is scored using appropriate software.

A histoscore is used as a more quantitative measure of the IHC data. The histoscore is calculated as follows:

$$\text{Histoscore}=[(\% \text{ tumor} \times 1(\text{low intensity}))+(\% \text{ tumor} \times 2(\text{medium intensity}))+(\% \text{ tumor} \times 3(\text{high intensity}))]$$

To determine the histoscore, the pathologist estimates the percentage of stained cells in each intensity category within a specimen. Because expression of most biomarkers is heterogeneous the histoscore is a truer representation of the overall expression. The final histoscore range is 0 (no expression) to 300 (maximum expression).

An alternative means of quantifying PD-L1 expression in a test tissue sample IHC is to determine the adjusted inflammation score (AIS) score defined as the density of inflammation multiplied by the percent PD-L1 expression by tumor-infiltrating inflammatory cells (Taube et al., *Sci. Transl. Med.* 4(127):127ra37 (2012)).

Anti-PD-1 Antibodies

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction mediates potent antitumor activity in preclinical models.

HuMAbs that bind specifically to PD-1 with high affinity have been disclosed in U.S. Pat. Nos. 8,008,449 and 8,779,105. Other anti-PD-1 mAbs have been described in, for example, U.S. Pat. Nos. 6,808,710, 7,488,802, 8,168,757 and 8,354,509, and PCT Publication No. WO 2012/145493. Each of the anti-PD-1 HuMAbs disclosed in U.S. Pat. No. 8,008,449 has been demonstrated to exhibit one or more of the following characteristics: (a) binds to human PD-1 with a $K_D$ of $1 \times 10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies useful for the present invention include mAbs that bind specifically to human PD-1 and exhibit at least one, at least two, at least three, at least four, or at least five of the preceding characteristics.

In one embodiment, the anti-PD-1 antibody is nivolumab. Nivolumab (also known as "OPDIVO®"; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., *Cancer Immunol Res.* 2(9):846-56 (2014)). In another embodiment, the anti-PD-1 antibody or fragment thereof cross-competes with nivolumab. In other embodiments, the anti-PD-1 antibody or fragment thereof binds to the same epitope as nivolumab. In certain embodiments, the anti-PD-1 antibody has the same CDRs as nivolumab.

In another embodiment, the anti-PD-1 antibody or fragment thereof cross-competes with pembrolizumab. In some embodiments, the anti-PD-1 antibody or fragment thereof binds to the same epitope as pembrolizumab. In certain embodiments, the anti-PD-1 antibody has the same CDRs as pembrolizumab. In another embodiment, the anti-PD-1 antibody is pembrolizumab. Pembrolizumab (also known as "KEYTRUDA®", lambrolizumab, and MK-3475) is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also cancer.gov/drugdictionary?cdrid=695789 (last accessed: Dec. 14, 2014). Pembrolizumab has been approved by the FDA for the treatment of relapsed or refractory melanoma.

In other embodiments, the anti-PD-1 antibody or fragment thereof cross-competes with MEDI0608. In still other embodiments, the anti-PD-1 antibody or fragment thereof binds to the same epitope as MEDI0608. In certain embodiments, the anti-PD-1 antibody has the same CDRs as MEDI0608. In other embodiments, the anti-PD-1 antibody is MEDI0608 (formerly AMP-514), which is a monoclonal antibody. MEDI0608 is described, for example, in U.S. Pat. No. 8,609,089B2 or in cancer.gov/drugdictionary?cdrid=756047 (last accessed Dec. 14, 2014).

In certain embodiments, the first antibody is an anti-PD-1 antagonist. One example of the anti-PD-1 antagonist is AMP-224, which is a B7-DC Fc fusion protein. AMP-224 is discussed in U.S. Publ. No. 2013/0017199 or in cancer.gov/publications/dictionaries/cancer-drug?cdrid=700595 (last accessed Jul. 8, 2015).

In other embodiments, the anti-PD-1 antibody or fragment thereof cross-competes with BGB-A317. In some embodiments, the anti-PD-1 antibody or fragment thereof binds the same epitope as BGB-A317. In certain embodiments, the anti-PD-1 antibody has the same CDRs as BGB-A317. In certain embodiments, the anti-PD-1 antibody is BGB-A317, which is a humanized monoclonal antibody. BGB-A317 is described in U.S. Publ. No. 2015/0079109.

In some embodiments, the antibody is Pidilizumab (CT-011), which is an antibody previously reported to bind to PD-1 but which is believed to bind to a different target. Pidilizumab is described in U.S. Pat. No. 8,686,119 B2 or WO 2013/014668 A1.

Anti-PD-1 antibodies useful for the disclosed compositions also include isolated antibodies that bind specifically to human PD-1 and cross-compete for binding to human PD-1 with nivolumab (see, e.g., U.S. Pat. Nos. 8,008,449 and 8,779,105; WO 2013/173223). The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar to those of nivolumab by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 as, nivolumab are mAbs. For administration to human subjects, these cross-competing antibodies can be chimeric antibodies, or humanized or human antibodies. Such chimeric, humanized or human mAbs can be prepared and isolated by methods well known in the art.

Anti-PD-1 antibodies useful for the compositions of the disclosed invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

Anti-PD-1 antibodies suitable for use in the disclosed compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and upregulating the immune system. In certain embodiments, the anti-PD-1 antibody or antigen-binding portion thereof cross-competes with nivolumab for binding to human PD-1. In other embodiments, the anti-PD-1 antibody or antigen-binding portion thereof is a chimeric, humanized or human monoclonal antibody or a portion thereof. In certain embodiments, the antibody is a humanized antibody. In other embodiments, the antibody is a human antibody. Antibodies of an IgG1, IgG2, IgG3 or IgG4 isotype can be used.

In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies (Wang et al., 2014 *Cancer Immunol Res.* 2(9):846-56). In yet other embodiments, the antibody comprises a light chain constant region which is a human kappa or lambda constant region. In other embodiments, the anti-PD-1 antibody or antigen-binding portion thereof is a mAb or an antigen-binding portion thereof. In certain embodiments of any of the therapeutic methods described herein comprising administration of an anti-PD-1 antibody, the anti-PD-1 antibody is nivolumab. In other embodiments, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0608 (formerly AMP-514), AMP-224, or BGB-A317.

Because anti-PD-1 and anti-PD-L1 target the same signaling pathway and have been shown in clinical trials to exhibit similar levels of efficacy in a variety of cancers, including RCC (see Brahmer et al. (2012) *N Engl J Med* 366:2455-65; Topalian et al. (2012a) *N Engl J Med* 366: 2443-54; WO 2013/173223), an anti-PD-L1 antibody may be substituted for the anti-PD-1 Ab in any of the therapeutic methods disclosed herein. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446) (see, e.g., Herbst et al. (2013) *J Clin Oncol* 31(suppl):3000. Abstract; U.S. Pat. No. 8,217,149) or MEDI4736 (Khleif (2013) In: Proceedings from the European Cancer Congress 2013; Sep. 27-Oct. 1, 2013; Amsterdam, The Netherlands. Abstract 802). In certain embodiments, the antibodies that cross-compete for binding to human PD-L1 with, or bind to the same epitope region of human PD-L1 as the above-references PD-L1 antibodies are mAbs. For administration to human subjects, these cross-competing antibodies can be chimeric antibodies, or can be humanized or human antibodies. Such chimeric, humanized or human mAbs can be prepared and isolated by methods well known in the art.

Anti-PD-L1 Antibodies

In certain embodiments, the present application encompasses use of an anti-PD-L1 antibody as a monotherapy in lieu of anti-PD-1 antibody. In one embodiment, the anti-PD-L1 antibody inhibits the binding of PD-L1 receptor, i.e., PD-1 to its ligand PD-L1.

Anti-PD-L1 antibodies useful for the invention include antibodies engineered starting from antibodies having one or more of the $V_H$ and/or $V_L$ sequences disclosed herein, which engineered antibodies can have altered properties from the starting antibodies. An anti-PD-L1 antibody can be engineered by a variety of modifications as described above for the engineering of modified anti-PD-1 antibodies of the invention.

Anti-PD-L1 antibodies of the invention also include isolated antibodies selected for their ability to bind to PD-L1 in formalin-fixed, paraffin-embedded (FFPE) tissue specimens. The use of FFPE samples is essential for the long-term follow-up analysis of the correlation between PD-L1 expression in tumors and disease prognosis or progression. The use of different antibodies to stain PD-L1 in frozen versus FFPE tissues, and the ability of certain antibodies to distinguish membranous and/or cytoplasmic forms of PD-L1, may account for some of the disparate data reported in the literature correlating PD-L1 expression with disease prognosis (Hamanishi et al., *Proc. Natl. Acad. Sci. USA* 104(9): 3360-3365 (2007); Gadiot et al., *Cancer* 117(10):2192-2201

(2011)). This disclosure provides several rabbit mAbs that bind with high affinity specifically to membranous human PD-L1 in FFPE tissue samples comprising tumor cells and tumor-infiltrating inflammatory cells.

In some embodiments, an anti-PD-L1 antibody useful for the present methods includes mAb 28-8 set forth in SEQ ID NOs. 1 and 2, respectively. The sequences of the heavy and light chain CDR domains of mAb 28-8, as delineated using the Kabat system, are set forth in SEQ ID NOs. 3-8. In other embodiments, an anti-PD-L1 antibody useful for the invention comprises mAbs 28-1, 28-12, 29-8 and 20-12 or an antigen-binding portion thereof, for example, including Fab, F(ab')$_2$ Fd, Fv, and scFv, di-scFv or bi-scFv, and scFv-Fc fragments, diabodies, triabodies, tetrabodies, and isolated CDRs.

Anti-CTLA-4 Antibodies

Anti-CTLA-4 antibodies of the instant invention bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

HuMAbs that bind specifically to CTLA-4 with high affinity have been disclosed in U.S. Pat. Nos. 6,984,720 and 7,605,238. Other anti-PD-1 mAbs have been described in, for example, U.S. Pat. Nos. 5,977,318, 6,051,227, 6,682, 736, and 7,034,121. The anti-PD-1 HuMAbs disclosed in U.S. Pat. Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7$ M$^{-1}$, or about $10^9$ M$^{-1}$, or about $10^{10}$ M$^{-1}$ to $10^{11}$ M$^{-1}$ or higher, as determined by Biacore analysis; (b) a kinetic association constant ($k_a$) of at least about $10^3$, about $10^4$, or about $10^5$ m$^{-1}$ s$^{-1}$; (c) a kinetic disassociation constant ($k_d$) of at least about $10^3$, about $10^4$, or about $10^5$ m$^{-1}$ s$^{-1}$; and (d) inhibits the binding of CTLA-4 to B7-1 (CD80) and B7-2 (CD86). Anti-CTLA-4 antibodies useful for the present invention include mAbs that bind specifically to human CTLA-4 and exhibit at least one, at least two, or at least three of the preceding characteristics.

An exemplary clinical anti-CTLA-4 antibody is the human mAb 10D1 (now known as ipilimumab and marketed as YERVOY®) as disclosed in U.S. Pat. No. 6,984,720. Ipilimumab is an anti-CTLA-4 antibody for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

Another anti-CTLA-4 antibody useful for the present methods is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

Anti-CTLA-4 antibodies useful for the disclosed composition also include isolated antibodies that bind specifically to human CTLA-4 and cross-compete for binding to human CTLA-4 with ipilimumab or tremelimumab or bind to the same epitope region of human CTLA-4 as ipilimumab or tremelimumab. In certain embodiments, the antibodies that cross-compete for binding to human CTLA-4 with, or bind to the same epitope region of human CTLA-4 as does ipilimumab or tremelimumab, are antibodies comprising a heavy chain of the human IgG1 isotype. For administration to human subjects, these cross-competing antibodies are chimeric antibodies, or humanized or human antibodies. Useful anti-CTLA-4 antibodies also include antigen-binding portions of the above antibodies such as Fab, F(ab')$_2$, Fd or Fv fragments.

Dosages

The anti-PD-1 antibody can be administered to a suitable patient in therapeutically effective amounts. For example, the anti-PD-1 antibody can be administered at a dosage ranging from at least about 0.1 to at least about 20.0 mg/kg body weight. In certain embodiments, the anti-PD-1 antibody is individually administered at a dosage of at least about 0.1, at least about 0.3, at least about 0.5, at least about 1, at least about 3, at least about 5, at least about 10 or at least about 20 mg/kg, e.g., at least about 1 to at least about 10 mg/kg, e.g., at least about 1 to at least about 3 mg/kg, e.g., at least about 3 mg/kg, e.g., at least about 1 mg/kg. The anti-PD-1 antibody can be administered at a dosing frequency of at least once about every week, at least once about every 2 weeks, at least once about every 3 weeks, or at least once about every 4 weeks, or at least once a month, for up to 6 to up to 72 doses, or for as long as clinical benefit is observed, or until unmanageable toxicity or disease progression occurs. In some embodiments, the anti-PD-1 antibody is administered at a dosage of about 1 or about 3 mg/kg. In certain embodiments, an anti-PD-1 antibody regimen comprises administering the anti-PD-1 antibody to the subject at a dosing frequency of once about every week, once about every 2 weeks, once about every 3 weeks, or once about every 4 weeks, or once a month for 6 to 72 doses, or for as long as clinical benefit is observed, or until unmanageable toxicity or disease progression occurs. In other embodiments, the anti-PD-1 antibody is administered at a dosage of about 1 mg/kg at a dosing frequency of once about every 3 weeks for up to 48 doses.

In other embodiments, the anti-PD-1 antibody is administered at the following dosages: (a) 0.1 mg/kg anti-PD-1 antibody; (b) 0.3 mg/kg anti-PD-1 antibody; (c) 1 mg/kg anti-PD-1 antibody; (d) 3 mg/kg anti-PD-1 antibody; (e) 5 mg/kg anti-PD-1 antibody; (f) 10 mg/kg anti-PD-1 antibody; (g) 0.1 mg/kg anti-PD-1 antibody; (h) 0.3 mg/kg anti-PD-1 antibody; (i) 1 mg/kg anti-PD-1 antibody; (j) 3 mg/kg anti-PD-1 antibody; (k) 5 mg/kg anti-PD-1 antibody; or (l) 10 mg/kg anti-PD-1 antibody. In a particular embodiment, the method includes administration of 1 mg/kg of an anti-PD-1 antibody.

In some embodiments, the dosage of the anti-PD-1 antibody is kept constant during the induction dosing schedule and the maintenance dosing schedule. In certain embodiments, a regimen comprises: (i) an induction dosing schedule comprising administration of the anti-PD-1 antibody at a dosing frequency of at least once about every 2 weeks, once about every 3 weeks, or once about every 4 weeks, or at least once a month, for at least 2, 4, 6, 8 or 10 doses, followed by administration of the anti-PD-1 antibody at a dosing frequency of at least once about every 2 weeks, once about every 3 weeks, or once about every 4 weeks, or at least once a month, for at least 2, 4, 6, 8 or 12 doses; followed by (ii) a maintenance dosing schedule comprising administration of the anti-PD-1 antibody at a dosing frequency of at least once about every 8 weeks, once about every 12 weeks, or once about every 16 weeks, or at least about once a quarter, for at least 4, 6, 8, 10, 12 or 16 doses, or for as long as clinical benefit is observed, or until unmanageable toxicity or disease progression occurs. In one particular embodiment, the dosing schedule comprises administering about 3 mg/kg of an anti-PD-1 antibody every 2 weeks. In another embodiment, the dosing schedule comprises administering about 1 mg/kg of an anti-PD-1 antibody every 3 weeks for 4 doses followed by about 3 mg/kg of an anti-PD-1 antibody every 2 weeks.

In certain embodiments of this method, the maintenance dosing schedule comprises combined administration of up to 4, 6, 8, 10, 12 or 16 doses of the anti-PD-1 antibody. In other embodiments, the concurrent regimen comprises: (i) an induction dosing schedule comprising administration of the anti-PD-1 antibody at a dosing frequency of once about every 2 weeks, once about every 3 weeks, or once about every 4 weeks, or once a month, for 2, 4, 6 or 8 doses, followed by administration of the anti-PD-1 antibody at a dosing frequency of once about every 2 weeks, once about every 3 weeks, or once about every 4 weeks, or once a month, for 2, 4, 6, 8 or 12 doses; followed by (ii) a maintenance dosing schedule comprising administration of the anti-PD-1 antibody at a dosing frequency of once about every 8 weeks, once about every 12 weeks, or once about every 16 weeks, or about once a quarter, for 4, 6, 8, 10, 12 or 16 doses, or for as long as clinical benefit is observed, or until unmanageable toxicity or disease progression occurs.

In a particular embodiment, the anti-PD-1 antibody is administered at dosages of about 1 mg/kg anti-PD-1 antibody every three weeks.

In certain embodiments of the present methods, the anti-PD-1 antibody is formulated for parenteral administration, e.g., intravenous administration.

In some embodiments, the therapeutically effective dosage of the anti-PD-1 antibody or antigen-binding portion thereof is a flat dosing (not a bodyweight based dosing) and comprises about 60 mg, about 80 mg, about 100 mg, about 120 mg, about 140 mg, about 160 mg, about 180 mg, about 200 mg, about 220 mg, about 240 mg, about 260 mg, about 280 mg, or about 300 mg. In other embodiments, the therapeutically effective dosage of the anti-PD-1 antibody or antigen-binding portion thereof comprises about 320 mg, 360 mg, 400 mg, 420 mg, 480 mg, 500 mg, 540 mg, 550 mg, 600 mg, 620 mg, 650 mg, 680 mg, 700 mg, 720 mg, 780 mg, 800 mg, 840 mg, or 900 mg. In some embodiments, the dose of the anti-PD-1 antibody in the composition is between about 60 mg and about 300 mg, between about 60 mg and about 100 mg, between about 100 mg and about 200 mg, or between about 200 mg and about 300 mg. In some embodiments, the amount of the anti-PD-1 antibody in the composition is at least about 80 mg, about 160 mg, or about 240 mg. In some embodiments, the dose of the anti-PD-1 antibody in the composition is at least about 240 mg or at least about 80 mg.

In other embodiments, the dosages are given every week, every two weeks, every three weeks, every four weeks, every five weeks, every six weeks, every seven weeks, every eight weeks, every nine weeks, or every 10 weeks.

In some embodiments, the anti-PD-1 antibody or antigen-binding portion thereof is administered at a dose of about 240 mg. In embodiments, the anti-PD-1 antibody or antigen-binding portion thereof is administered at a dose of about 360 mg. In embodiments, the anti-PD-1 antibody or antigen-binding portion thereof is administered at a dose of about 480 mg. In one embodiment, 360 mg of the anti-PD-1 antibody or antigen binding fragment is administered once every 3 weeks. In another embodiment, 480 mg of the anti-PD-1 antibody or antigen binding fragment is administered once every 4 weeks.

The combination of an anti-PD-1 antibody and an anti-CTLA-4 antibody can be administered to a suitable patient in therapeutically effective amounts. For example, each antibody can be administered at a dosage ranging from at least about 0.1 to at least about 20.0 mg/kg body weight. In certain embodiments, each of the anti-PD-1 and anti-CTLA-4 antibodies is individually administered at a dosage of at least about 0.1, at least about 0.3, at least about 0.5, at least about 1, at least about 3, at least about 5, at least about 10 or at least about 20 mg/kg, e.g., at least about 1 to at least about 10 mg/kg, e.g., at least about 1 to at least about 3 mg/kg, e.g., at least about 3 mg/kg, e.g., at least about 1 mg/kg. Each of the anti-PD-1 antibody and anti-CTLA-4 antibody can be administered at a dosing frequency of at least once about every week, at least once about every 2 weeks, at least once about every 3 weeks, or at least once about every 4 weeks, or at least once a month, for up to 6 to up to 72 doses, or for as long as clinical benefit is observed, or until unmanageable toxicity or disease progression occurs. In some embodiments, the anti-PD-1 antibody is administered at a dosage of about 1 or about 3 mg/kg. In certain embodiments, the sequenced regimen comprises administering the anti-PD-1 antibody to the subject at a dosing frequency of once about every week, once about every 2 weeks, once about every 3 weeks, or once about every 4 weeks, or once a month for 6 to 72 doses, or for as long as clinical benefit is observed, or until unmanageable toxicity or disease progression occurs. In other embodiments, the anti-PD-1 is administered at a dosage of about 1 mg/kg at a dosing frequency of once about every 3 weeks for up to 48 doses. In some embodiments, the anti-CTLA-4 antibody is administered at a dosage of 1 or 3 mg/kg. In certain embodiments, the sequenced regimen comprises administering the anti-CTLA-4 antibody to the subject at a dosing frequency of once about every week, once about every 2 weeks, once about every 3 weeks, or once about every 4 weeks, or once a month for 6 to 72 doses, or for as long as clinical benefit is observed, or until unmanageable toxicity or disease progression occurs. In other embodiments, the anti-CTLA-4 antibody is administered at a dosage of about 3 mg/kg at a dosing frequency of once about every 3 weeks for up to 48 doses.

In other embodiments, the anti-PD-1 and anti-CTLA-4 antibodies are administered at the following dosages: (a) 0.1 mg/kg anti-PD-1 antibody and 3 mg/kg of anti-CTLA-4 antibody; (b) 0.3 mg/kg anti-PD-1 antibody and 3 mg/kg of anti-CTLA-4 antibody; (c) 1 mg/kg anti-PD-1 antibody and 3 mg/kg of anti-CTLA-4 antibody; (d) 3 mg/kg anti-PD-1 A antibody b and 3 mg/kg of anti-CTLA-4 antibody; (e) 5 mg/kg anti-PD-1 antibody and 3 mg/kg of anti-CTLA-4 antibody; (f) 10 mg/kg anti-PD-1 antibody and 3 mg/kg of anti-CTLA-4 antibody; (g) 0.1 mg/kg anti-PD-1 antibody and 1 mg/kg of anti-CTLA-4 antibody; (h) 0.3 mg/kg anti-PD-1 antibody and 1 mg/kg of anti-CTLA-4 antibody; (i) 1 mg/kg anti-PD-1 antibody and 1 mg/kg of anti-CTLA-4 antibody; (j) 3 mg/kg anti-PD-1 antibody and 1 mg/kg of anti-CTLA-4 antibody; (k) 5 mg/kg anti-PD-1 antibody and 1 mg/kg of anti-CTLA-4 antibody; or (l) 10 mg/kg anti-PD-1 antibody and 1 mg/kg of anti-CTLA-4 antibody. In a particular embodiment, the methods include administration of 1 mg/kg of an anti-PD-1 antibody and 3 mg/kg of an anti-CTLA-4 antibody.

In some embodiments, the dosage of each of the anti-PD-1 and anti-CTLA-4 antibodies is kept constant during the induction dosing schedule and the maintenance dosing schedule. In certain embodiments, a regimen comprises: (i) an induction dosing schedule comprising combined administration of the anti-PD-1 and anti-CTLA-4 antibodies at a dosing frequency of at least once about every 2 weeks, once about every 3 weeks, or once about every 4 weeks, or at least once a month, for at least 2, 4, 6, 8 or 10 doses, followed by administration of the anti-PD-1 antibody alone at a dosing frequency of at least once about every 2 weeks, once about every 3 weeks, or once about every 4 weeks, or at least once a month, for at least 2, 4, 6, 8 or 12 doses; followed by (ii) a maintenance dosing schedule comprising combined administration of the anti-PD-1 and anti-CTLA-4 antibodies at a dosing frequency of at least once about every 8 weeks, once about every 12 weeks, or once about every 16 weeks, or at least about once a quarter, for at least 4, 6, 8, 10, 12 or 16 doses, or for as long as clinical benefit is observed, or until unmanageable toxicity or disease progression occurs.

In certain embodiments of this method, the maintenance dosing schedule comprises combined administration of up to 4, 6, 8, 10, 12 or 16 doses of the anti-PD-1 and anti-CTLA-4 antibodies. In other embodiments, the concurrent regimen comprises: (i) an induction dosing schedule comprising combined administration of the anti-PD-1 and anti-CTLA-4 antibodies at a dosing frequency of once about every 2 weeks, once about every 3 weeks, or once about every 4 weeks, or once a month, for 2, 4, 6 or 8 doses, followed by administration of the anti-PD-1 antibody alone at a dosing frequency of once about every 2 weeks, once about every 3 weeks, or once about every 4 weeks, or once a month, for 2, 4, 6, 8 or 12 doses; followed by (ii) a maintenance dosing schedule comprising combined administration of the anti-PD-1 and anti-CTLA-4 antibodies at a dosing frequency of once about every 8 weeks, once about every 12 weeks, or once about every 16 weeks, or about once a quarter, for 4, 6, 8, 10, 12 or 16 doses, or for as long as clinical benefit is observed, or until unmanageable toxicity or disease progression occurs.

In a particular embodiment, the anti-PD-1 and anti-CTLA-4 antibodies are administered at dosages of about 1 mg/kg anti-PD-1 antibody every three weeks and about 3 mg/kg of anti-CTLA-4 antibody every three weeks.

In certain embodiments of the present methods, the anti-PD-1 and anti-CTLA-4 antibodies are formulated for parenteral administration, e.g., intravenous administration. In certain other embodiments, when the anti-PD-1 and anti-CTLA-4 antibodies are administered in combination, they are administered within about 30 minutes of each other. Either antibody may be administered first, that is, in certain embodiments, the anti-PD-1 antibody is administered before the anti-CTLA-4 antibody, whereas in other embodiments, the anti-CTLA-4 antibody is administered before the anti-PD-1 antibody. Typically, each antibody is administered intravenously over a period of about 60 minutes. In further embodiments, the anti-PD-1 and anti-CTLA-4 antibodies are administered concurrently, either admixed as a single composition in a pharmaceutically acceptable formulation for concurrent administration, or concurrently as separate compositions with each antibody in a pharmaceutically acceptable formulation.

In some embodiments, the anti-PD-1 antibody and the anti-CTLA-4 antibody are formulated in a single composition. The ratio of the amount of the anti-PD-1 antibody and the amount of the anti-CTLA-4 antibody in the single composition can be 10:1 to 1:10. In other embodiments, the ratio of the amount of the anti-PD-1 antibody and the amount of the anti-CTLA-4 antibody in the single composition is 5:1, 4:1, 3:1, 2:1, 1:1, 1:2, 1:3, 1:4, or 1:5. In a particular embodiment, the ratio of the amount of the anti-PD-1 antibody and the amount of the anti-CTLA-4 antibody in the single composition is 1:3.

In some embodiments, the composition is administered at a flat dose regardless of the weight of the patient. For example, each of the anti-PD-1 antibody with the anti-CTLA-4 antibody may be administered at a flat dose of 20, 50, 75, 80, 160, 200, 240, 300, 360, 400, 480, 500, 750 or 1500 mg, without regard to the patient's weight. In some embodiments the composition is administered at a weight-based dose at any dose disclosed herein. In some embodiments, the amount of the anti-PD-1 antibody and the amount of the anti-CTLA-4 antibody administered to the patient at a single dose are identical.

In other embodiments, the therapeutically effective dosage of the anti-CTLA-4 antibody or antigen-binding portion thereof comprises about 60 mg, about 80 mg, about 100 mg, about 120 mg, about 140 mg, about 160 mg, about 180 mg, about 200 mg, about 220 mg, about 240 mg, about 260 mg, about 280 mg, or about 300 mg. In some embodiments, the dose of the anti-CTLA-4 antibody in the composition is between about 60 mg and about 300 mg, between about 60 mg and about 100 mg, between about 100 mg and about 200 mg, or between about 200 mg and about 300 mg. In some embodiments, the amount of the anti-CTLA-4 antibody in the composition is at least about 80 mg, about 160 mg, or about 240 mg. In some embodiments, the dose of the anti-CTLA-4 antibody in the composition is at least about 240 mg or at least about 80 mg.

In some embodiments, a flat dose of an anti-PD-1 antibody is 80 mg, and a flat dose of an anti-CTLA-4 antibody is 240 mg.

In some embodiments, the anti-PD-1 antibody is administered at a subtherapeutic dose, i.e., a dose of the therapeutic agent that is significantly lower than the usual or FDA-approved dose when administered as monotherapy for the treatment of the cancer. The quantity of the second antibody in the composition is calculated based on the desired ratio.

In some embodiments, the composition is administered by intravenous infusion about once per week, about once every 2 weeks, about once every 3 weeks, or about once a month. In certain embodiments, the composition is administered once every 3 weeks. In some embodiments, the infusion occurs over at least about 10 minutes, about 20 minutes, about 30 minutes, about 45 minutes, about 60 minutes, about 90 minutes, about 2 hours, about 3 hours, about 4 hours or about 5 hours.

Actual dosage levels of the active ingredients in the pharmaceutical compositions of the present invention can be flat or varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

Kits

Also within the scope of the present invention are kits, including pharmaceutical kits, comprising an anti-PD-1 antibody, for therapeutic uses, and diagnostic kits comprising an anti-PD-L1 antibody for assaying membranous PD-L1 expression as a biomarker for screening patients for the combination therapy or for predicting the efficacy of the anti-PD-1 monotherapy. In some embodiments, the pharmaceutical kits further comprise a combination of an anti-PD-1 antibody and an anti-CTLA-4 Ab, for therapeutic uses. Kits typically include a label indicating the intended use of the contents of the kit and instructions for use. The term "label" includes any writing, or recorded material supplied on or with the kit, or which otherwise accompanies the kit. In certain embodiments of a pharmaceutical kit, the anti-PD-1 antibody is co-packaged with an anti-CTLA-4 antibody in unit dosage form. In certain embodiments of a diagnostic kit, the anti-PD-L1 antibody is co-packaged with an anti-PD-1 antibody for performing an assay to detect and/or quantify PD-L1 expression. In one particular embodiment, the diagnostic kit further comprises an anti-CTLA-4 antibody.

In certain embodiments, the pharmaceutical kit comprises the anti-human PD-1 HuMAb, nivolumab. In other embodiments, the pharmaceutical kit comprises the anti-human PD-L1 HuMAb, BMS-936559. In yet other embodiments, the pharmaceutical kit comprises the anti-human CTLA-4 HuMAb, ipilimumab. In certain embodiments, the diagnostic kit comprises the rabbit anti-human PD-L1 mAb, 28-8, comprising the $V_H$ and $V_L$ regions whose amino acid sequences are set forth in SEQ ID NOs. 1 and 2, respectively. In other embodiments, the diagnostic kit comprises the murine anti-human PD-L1 mAb, 5H1 (Dong et al., *Nature Med.* 8(8):793-800 (2002)).

In some embodiments, the invention provides a kit for treating a patient afflicted with a melanoma tumor, the kit comprising:
(a) a dosage ranging from at least about 0.1 to at least about 10 mg/kg body weight of an anti-PD-1 antibody or an antigen-binding portion thereof; and
(b) instructions for using the anti-PD-1 antibody or the antigen-binding portion thereof in the methods disclosed herein.

In another embodiment, the invention provides a kit for treating a patient afflicted with a melanoma tumor, the kit comprising:
(a) a dosage ranging from at least about 0.1 to at least about 10 mg/kg body weight of an anti-PD-1 antibody or an antigen-binding portion thereof;
(b) a dosage ranging from at least about 0.1 to at least about 10 mg/kg body weight of an anti-CTLA-4 antibody or an antigen-binding portion thereof; and
(c) instructions for using the anti-PD-1 antibody or the antigen-binding portion thereof and the anti-CTLA-4 antibody or the antigen-binding portion thereof in the methods disclosed herein.

The present invention is further illustrated by the following examples which should not be construed as further limiting. The contents of all references cited throughout this application are expressly incorporated herein by reference.

EXAMPLES

Example 1

A randomized, double-blind, multicenter, phase 3 trial was conducted to evaluate the safety and efficacy of nivolumab alone or nivolumab combined with ipilimumab in comparison with ipilimumab alone in previously untreated metastatic melanoma.

Patients

Eligible patients had histologically confirmed stage III (unresectable) or stage IV melanoma, and no prior systemic treatment for unresectable or metastatic melanoma. Other eligibility criteria included an age of at least 18 years, an Eastern Cooperative Oncology Group (ECOG) performance status score of 0 (indicating no symptoms) or 1 (indicating mild symptoms), measurable disease by computed tomography or magnetic resonance imaging per RECIST v1.1, availability of tissue collected from metastatic or unresectable tumors for the assessment of PD-L1 status, and known BRAF V600 mutation status (or consent to BRAF V600 mutation testing per local standards). Key exclusion criteria were presence of active brain metastases, ocular melanoma, or autoimmune disease, and any prior treatment with an anti-PD-1, anti-PD-L1, anti-PD-L2, or anti-CTLA-4 antibody. Patients who required systemic corticosteroid treatment or other immunosuppressive medications within 14 days of study drug administration were excluded.

Study Design and Treatment

In the double-blind, phase 3 study, enrolled patients were randomly assigned in a 1:1:1 ratio to receive 3 mg of nivolumab per kilogram of body weight every 2 weeks (plus ipilimumab-matched placebo), or 1 mg of nivolumab per kilogram every 3 weeks plus 3 mg of ipilimumab per kilogram every 3 weeks for 4 doses (plus nivolumab-matched placebo), followed by 3 mg of nivolumab per kilogram every 2 weeks for cycle 3 and beyond, or 3 mg of ipilimumab per kilogram every 3 weeks for 4 doses (plus nivolumab-matched placebo).

Both nivolumab and ipilimumab were administered by intravenous infusion. Randomization was stratified according to tumor PD-L1 status (positive vs. negative or indeterminate), BRAF mutation status (V600 mutation positive vs. wild-type), and American Joint Committee on Cancer metastasis stage (M0, M1a, or M1b vs. M1c). Treatment continued until RECIST v1.1-defined disease progression, unacceptable toxicity, or withdrawal of consent. Patients could be treated beyond progression provided they had a clinical benefit without clinical deterioration, and did not have substantial adverse effects, as assessed by the investigator.

Progression-free survival and overall survival were co-primary end points. Secondary end points included objective response rate, tumor PD-L1 expression as a predictive biomarker for progression-free and overall survival, and health-related quality of life. Exploratory end points include duration of objective response and safety/tolerability of study drug therapy.

Assessments

Patients were assessed for tumor response, according to RECIST v1.1 at 12 weeks after randomization and continuing every 6 weeks for 49 weeks, and then every 12 weeks until progression or treatment discontinuation, whichever occurred later. Progression-free survival was defined as the time between the date of randomization and the first date of documented progression or death, whichever occurred first. Patients treated beyond progression were considered to have progressive disease at the time of the initial progression event, as assessed by the investigator, regardless of subsequent tumor responses. Expression of PD-L1 on the surface of the tumor cells was assessed in a central laboratory by immunohistochemistry in formalin-fixed, paraffin-embedded tumor specimens using a rabbit monoclonal anti-human PD-L1 antibody (clone 28-8) and an analytically validated automated assay developed by Dako (Carpinteria, CA). PD-L1 positivity was defined as at least 5% of tumor cells showing cell surface PD-L1 staining of any intensity in a section containing at least 100 tumor cells that could be evaluated. Indeterminate status was attributed to samples for which tumor cell-surface expression could not be discerned because of melanin content or strong cytoplasmic staining.

Any patient who received at least one dose of study drug in each of the 3 treatment groups was included in the assessment of safety. The severity of adverse events was graded according to the National Cancer Institute Common Terminology Criteria for Adverse Events, version 4.0.18. Safety assessments were made continuously during the treatment phase, and up to 100 days after the last dose of study drug.

Statistical Analysis

A study sample size of approximately 915 patients, randomized to the 3 treatment arms in a 1:1:1 ratio, was planned. For the comparison of progression-free survival, the number of events projected to be observed at a follow-up of at least 9 months provided approximately 83% power to detect an average hazard ratio of 0.71 with a type I error of 0.005 (two-sided). Progression-free survival was compared between nivolumab plus ipilimumab and ipilimumab alone, and between nivolumab alone and ipilimumab alone with the use of a two-sided log-rank test stratified according to PD-L1 status, BRAF mutation status, and metastasis stage (as described above). The study was not designed for a formal statistical comparison between the nivolumab alone and nivolumab plus ipilimumab groups. Hazard ratios and corresponding two-sided 99.5% confidence intervals (CIs) were estimated using a Cox proportional hazards model, with treatment group as a single covariate, stratified by the above factors. Progression-free survival curves, medians with 95% CIs, and progression-free survival rates at 6, 12, and 18 months with 95% CIs were estimated using Kaplan-Meier methodology. Overall survival will be analyzed when all patients have a minimum follow-up of 22 months.

Results

Patients and Treatment

From July 2013 through March 2014, a total of 1296 patients were enrolled at 137 centers in Australia, Europe, Israel, New Zealand, and North America. A total of 945 patients underwent randomization: 316 patients were assigned to the nivolumab group, 314 to the nivolumab plus ipilimumab group, and 315 to the ipilimumab group (FIG. 1). Baseline characteristics were balanced across the three groups. A total of 58.0% had stage M1c disease, 36.1% had an elevated lactate dehydrogenase level, 31.5% had a BRAF mutation, and 26.5% had positive PD-L1 status (Table 1).

All randomized patients had been followed for a minimum of 9 months at the time of database lock (Feb. 17, 2015); 117 of 313 patients (37.4%) in the nivolumab group, 93 of 313 patients (29.7%) in the nivolumab plus ipilimumab group, and 50 of 311 patients (16.1%) in the ipilimumab group were continuing study treatment (Table 2). The most frequent reason for discontinuation was disease progression in the nivolumab and ipilimumab monotherapy groups (154 of 313 patients [49.2%] and 202 of 311 patients [65.0%], respectively), versus study drug toxicity in the nivolumab plus ipilimumab group (120 of 313 patients [38.3%]). The number of patients who had died was 85 (27.2%) in the nivolumab group, 86 (27.5%) in the nivolumab plus ipilimumab group, and 114 (36.7%) in the ipilimumab group.

The median number of doses in patients who received nivolumab alone or ipilimumab alone was 15 (range 1-38) and 4 (1-4), respectively. In the combination group, the median number of doses was 4 (range 1-39) for nivolumab and 4 (range 1-4) for ipilimumab; 147 of 313 patients (47%) received four or more doses of nivolumab monotherapy after combination treatment.

TABLE 1

| Characteristic | Nivolumab alone (N = 316) | Nivolumab plus Ipilimumab (N = 314) | Ipilimumab alone (N = 315) | Total (N = 945) |
|---|---|---|---|---|
| Age—yr | | | | |
| Mean | 58.7 | 59.3 | 60.8 | 59.6 |
| Range | 25-90 | 18-88 | 18-89 | 18-90 |
| Age groups—no. (%) | | | | |
| <65 yr | 198 (62.7) | 185 (58.9) | 182 (57.8) | 565 (59.8) |
| ≥65, <75 yr | 79 (25.0) | 94 (29.9) | 89 (28.3) | 262 (27.7) |
| ≥75 yr | 39 (12.3) | 35 (11.1) | 44 (14.0) | 118 (12.5) |
| Sex—no. (%) | | | | |
| Male | 202 (63.9) | 206 (65.6) | 202 (64.1) | 610 (64.6) |
| Female | 114 (36.1) | 108 (34.4) | 113 (35.9) | 335 (35.4) |
| ECOG performance status—no. (%) | | | | |
| 0 | 238 (75.3) | 230 (73.2) | 224 (71.1) | 692 (73.2) |
| 1 | 77 (24.4) | 83 (26.4) | 91 (28.9) | 251 (26.6) |
| 2 | 1 (0.3) | 0 | 0 | 1 (0.1) |
| Not reported | 0 | 1 (0.3) | 0 | 1 (0.1) |
| M stage—no. (%) | | | | |
| M1c | 184 (58.2) | 181 (57.6) | 183 (58.1) | 548 (58.0) |
| M0, M1a, or M1b | 132 (41.8) | 133 (42.4) | 132 (41.9) | 397 (42.0) |
| Lactate dehydrogenase—no. (%)* | | | | |
| ≤ULN | 196 (62.0) | 199 (63.4) | 194 (61.6) | 589 (62.3) |
| >ULN | 112 (35.4) | 114 (36.3) | 115 (36.5) | 341 (36.1) |

Baseline Characteristics of the Patients.

TABLE 1-continued

Baseline Characteristics of the Patients.

| Characteristic | Nivolumab alone (N = 316) | Nivolumab plus Ipilimumab (N = 314) | Ipilimumab alone (N = 315) | Total (N = 945) |
|---|---|---|---|---|
| ≤2 × ULN | 271 (85.8) | 276 (87.9) | 279 (88.6) | 826 (87.4) |
| >2 × ULN | 37 (11.7) | 37 (11.8) | 30 (9.5) | 104 (11.0) |
| Unknown | 8 (2.5) | 1 (0.3) | 6 (1.9) | 15 (1.6) |
| Brain metastases at baseline—no. (%) | | | | |
| Yes | 8 (2.5) | 11 (3.5) | 15 (4.8) | 34 (3.6) |
| No | 308 (37.5) | 303 (96.5) | 300 (95.2) | 911 (96.4) |
| PD-L1 status—no. (%) | | | | |
| Positive | 80 (27.8) | 68 (24.5) | 75 (27.1) | 223 (26.4) |
| Negative | 208 (72.2) | 210 (75.5) | 202 (72.9) | 620 (73.5) |
| BRAF status—no. (%) | | | | |
| Mutation | 100 (31.6) | 101 (32.2) | 97 (30.8) | 298 (31.5) |
| No mutation | 216 (68.4) | 213 (67.8) | 218 (69.2) | 647 (68.5) |

*ULN denotes upper limit of normal.

Efficacy

The median progression-free survival was 6.5 months (95% confidence interval [CI], 4.3 to 9.5) in the nivolumab group, 11.5 months (95% CI, 8.9 to 16.5) in the nivolumab plus ipilimumab group, and 2.9 months (95% CI, 2.8 to 3.4) in the ipilimumab group (FIG. 2A). A significant improvement in progression-free survival was observed in the nivolumab plus ipilimumab group as compared with the ipilimumab group (hazard ratio, 0.42; 95% CI, 0.31 to 0.57; P<0.0001) (FIG. 2A). A significant improvement in progression-free survival was also observed in the nivolumab group as compared with the ipilimumab group (hazard ratio, 0.57; 95% CI, 0.43 to 0.76; P<0.00001) (FIG. 2A). The hazard ratio for the comparison between nivolumab plus ipilimumab and nivolumab groups was 0.74 (95% CI, 0.60 to 0.92).

Analyses of progression-free survival among prespecified patient subgroups showed a consistent improvement with nivolumab or nivolumab plus ipilimumab as compared with ipilimumab, including subgroups defined by PD-L1 status, BRAF mutation status, and metastasis stage (FIGS. 3A and 3B). In the combination group, median PFS was 11.7 months (95% CI, 8.0 to not reached) among patients with a BRAF mutation and was 11.2 months (95% CI, 8.3 to not reached) in patients with wild-type BRAF (FIG. 3B). For patients with a positive PD-L1 tumor status, median progression-free survival in the nivolumab, nivolumab plus ipilimumab, and ipilimumab groups was 14.0 months (95% CI, 9.1 to not reached), 14.0 months (95% CI, 9.7 to not reached), and 3.9 months (95% CI, 2.8 to 4.2), respectively (FIG. 2B). For patients with a negative PD-L1 tumor status, median progression-free survival in the nivolumab, nivolumab plus ipilimumab, and ipilimumab groups was 5.3 months (95% CI, 2.8 to 7.1 months), 11.2 months (95% CI, 8.0 to not reached) and 2.8 months (95% CI, 2.8 to 3.1), respectively (FIG. 2C).

Investigator-assessed objective response rates were 43.7% (95% CI, 38.1 to 49.3%), 57.6% (95% CI, 52.0 to 63.2), and 19.0% (95% CI, 14.9 to 23.8) in the nivolumab, nivolumab plus ipilimumab, and ipilimumab groups, respectively (Table 3). The percentage of patients with a complete response was higher in the nivolumab plus ipilimumab group than in either the nivolumab or ipilimumab alone groups (11.5% vs. 8.9% and 2.2%) (Table 3). Time to objective response was similar in each group (Table 3), and the median duration of response was not reached in any of the groups.

Median reduction in the sum of the longest diameters of tumor target lesions was −34.5% (interquartile range: −75.4 to 15.4), −51.1% (−75.8 to −10.2), and 5.8% (−28.0 to 33.3) in the nivolumab, nivolumab plus ipilimumab, and ipilimumab groups, respectively (FIG. 4). Among patients with PD-L1-positive tumors, the objective response rates were 57.5% (95% CI, 45.9 to 68.5), 72.1% (95% CI, 59.9 to 82.3), and 21.3% (95% CI, 12.7 to 32.3) for the nivolumab, nivolumab plus ipilimumab, and ipilimumab groups, respectively; in patients with PD-L1-negative tumors, the objective response rates were 41.3% (95% CI, 34.6 to 48.4), 54.8% (95% CI, 47.8 to 61.6), and 17.8% (95% CI, 12.8 to 23.8) (Table 4).

Adverse Events

Treatment-related adverse events of any grade occurred in 82.1%, 95.5%, and 86.2% of patients in the nivolumab, nivolumab plus ipilimumab groups, and ipilimumab groups, respectively (Table 5). The most common adverse events in the nivolumab group were fatigue (in 34.2% of patients), rash (in 21.7%), and diarrhea (in 19.2%). In the nivolumab plus ipilimumab and ipilimumab groups, diarrhea (in 44.1% and 33.1% of patients, respectively), fatigue (in 35.1% and 28.0%), and pruritus (in 33.2% and 35.4%) were most common (Table 5). The incidence of treatment-related adverse events of grade 3 or 4 was also higher in the nivolumab plus ipilimumab group than in either the nivolumab or ipilimumab groups (55.0% vs. 16.3% and 27.3%), with diarrhea being the most common (2.2%, 9.3%, and 6.1% in the nivolumab, nivolumab plus ipilimumab, and ipilimumab groups, respectively) (Table 5). Treatment-related adverse events of any grade leading to discontinuation occurred in 7.7%, 36.4%, and 14.8% of patients in the nivolumab, nivolumab plus ipilimumab, and ipilimumab groups, respectively, with the most common being diarrhea (in 1.9%, 8.3%, and 4.5%, respectively) and colitis (in 0.6%, 8.3%, and 7.7%, respectively) (Table 5). One death due to study-drug toxicity was reported in the nivolumab group (neutropenia) and one in the ipilimumab group (cardiac arrest), although such adverse events have not been associated with these drugs in prior studies. No treatment-related deaths were reported in the combination group.

TABLE 2

| Patient Disposition.* | | | |
| --- | --- | --- | --- |
| | Nivolumab alone (N = 313) | Nivolumab plus Ipilimumab (N = 313) | Ipilimumab alone (N = 311) |
| Patients in the treatment period—no. (%) | | | |
| Continuing | 117 (37.4) | 93 (29.7) | 50 (16.1) |
| Not continuing | 196 (62.6) | 220 (70.3) | 261 (83.9) |
| Reason for not continuing the treatment—no. (%) | | | |
| Disease progression | 154 (49.2) | 69 (22.0) | 202 (65.0) |
| Study drug toxicity | 27 (8.6) | 120 (38.3) | 47 (15.1) |
| Adverse event unrelated to study drug | 5 (1.6) | 12 (3.8) | 4 (1.3) |
| Patient request to discontinue treatment | 5 (1.6) | 5 (1.6) | 4 (1.3) |
| Death | 5 (1.6) | 5 (1.6) | 4 (1.3) |

TABLE 2-continued

| Patient Disposition.* | | | |
| --- | --- | --- | --- |
| | Nivolumab alone (N = 313) | Nivolumab plus Ipilimumab (N = 313) | Ipilimumab alone (N = 311) |
| Maximum clinical benefit | 2 (0.6) | 2 (0.6) | 0 |
| Poor/non-compliance | 1 (0.3) | 1 (0.3) | 1 (0.3) |
| Patient withdrew consent | 0 | 3 (1.0) | 0 |
| Lost to follow-up | 1 (0.3) | 0 | 0 |
| Patient no longer meets study criteria | 0 | 1 (0.3) | 0 |
| Other | 0 | 3 (1.0) | 2 (0.6) |
| Patients in the study—no. (%) | | | |
| Continuing | 223 (71.2) | 221 (70.6) | 189 (60.8) |
| Died | 85 (27.2) | 86 (27.5) | 114 (36.7) |
| Not continuing | 5 (1.6) | 6 (1.9) | 8 (2.6) |

*At the time of database lock on Feb. 17, 2015.

TABLE 3

| Response to Treatment. | | | |
| --- | --- | --- | --- |
| Response | Nivolumab alone (N = 316) | Nivolumab plus Ipilimumab (N = 314) | Ipilimumab alone (N = 315) |
| Best overall response—no. (%)[†] | | | |
| Complete response | 28 (8.9) | 36 (11.5) | 7 (2.2) |
| Partial response | 110 (34.8) | 145 (46.2) | 53 (16.8) |
| Stable disease | 34 (10.8) | 41 (13.1) | 69 (21.9) |
| Progressive disease | 119 (37.7) | 71 (22.6) | 154 (48.9) |
| Could not be determined | 25 (7.9) | 21 (6.7) | 32 (10.2) |
| Objective response[‡] | | | |
| No. of patients (% [95% CI]) | 138 (43.7 [38.1-49.3]) | 181 (57.6 [52.0-63.2]) | 60 (19.0 [14.9-23.8]) |
| Estimated odds ratio (95% CI)[§] | 3.40 (2.02-5.72) | 6.11 (3.59-10.38) | — |
| Two-sided P value | <0.00001 | <0.00001 | — |
| Time to objective response—mo | | | |
| No. of responders | 138 | 181 | 60 |
| Median | 2.78 | 2.76 | 2.79 |
| Range | 2.3-12.5 | 1.1-11.6 | 2.5-12.4 |

[†]Best overall response were assessed by the investigators with the use of RECIST v1.1.
[‡]Data include patients with a complete response and those with a partial response.
[§]Relative to ipilimumab alone.

TABLE 4

| Objective Response Rate by PD-L1 Status. | | | |
| --- | --- | --- | --- |
| PD-L1 Positive | | | |
| Objective response[†] | Nivolumab alone (N = 80) | Nivolumab plus Ipilimumab (N = 68) | Ipilimumab alone (N = 75) |
| No. of patients (% [95% CI]) | 46 (57.5 [45.9-68.5]) | 49 (72.1 [59.9-82.3]) | 16 (21.3 [12.7-32.3]) |
| Estimated odds ratio (95% CI)[§] | 5.03 (2.44-10.37) | 10.41 (4.63-23.40) | — |
| PD-L1 Negative | | | |
| Objective response[†] | Nivolumab alone (N = 208) | Nivolumab plus Ipilimumab (N = 210) | Ipilimumab alone (N = 202) |
| No. of patients (% [95% CI]) | 86 (41.3 [34.6-48.4]) | 115 (54.8 [47.8-61.6]) | 36 (17.8 [12.8-23.8]) |
| Estimated odds ratio (95% CI)[§] | 3.25 (2.05-5.13) | 5.90 (3.71-9.38) | — |

[†]Best overall response was assessed by the investigators with the use of RECIST v1.1.
[§]Relative to ipilimumab alone.

The most frequent grade 3 or 4 treatment-related select adverse events were diarrhea (2.2%, 9.3%, and 6.1% of patients in the nivolumab, nivolumab plus ipilimumab, and ipilimumab groups, respectively), colitis (in 0.6%, 7.7%, and 8.7%, respectively), increased alanine aminotransferase (in 1.3%, 8.3%, and 1.6%, respectively), and increased aspartate aminotransferase (in 1.0%, 6.1%, and 0.6%, respectively) (Table 6). With the use of immune modulatory agents, resolution rates for grade 3 or 4 select adverse events were generally similar across treatment groups, and were between 85-100% across organ categories in the nivolumab plus ipilimumab group. As observed in prior studies, most endocrine events in all treatment groups did not resolve (Table 7).

Discussion

In this randomized, double-blind, phase 3 study, both nivolumab alone and the combination of nivolumab and ipilimumab significantly increased progression-free survival and objective response rates, as compared with ipilimumab alone, in previously untreated advanced melanoma. These results were observed independently of PD-L1 tumor status, BRAF mutation status, or metastasis stage. Baseline characteristics of study participants were typical of patients with advanced melanoma, although the BRAF mutation rate (31.5%) was lower than the 40-50% generally reported for advanced disease. While not a primary end point of the study, the combination of nivolumab and ipilimumab resulted in numerically longer progression-free survival and a higher response rate as compared with nivolumab alone in the overall study population. While time to response was similar between groups, the first tumor assessment was done at week 12 and thus the possibility that responses may have occurred earlier with the combination remains unknown.

TABLE 5

| | Adverse Events (Safety Population).* | | | | | |
|---|---|---|---|---|---|---|
| | Nivolumab alone (N = 313) | | Nivolumab plus Ipilimumab (N = 313) | | Ipilimumab alone (N = 311) | |
| Event | Total | Grade 3 or 4 | Total | Grade 3 or 4 | Total | Grade 3 or 4 |
| | no. of patients with event (%) | | | | | |
| Any adverse event | 311 (99.4) | 136 (43.5) | 312 (99.7) | 215 (68.7) | 308 (99.0) | 173 (55.6) |
| Treatment-related adverse event[†] | 257 (82.1) | 51 (16.3) | 299 (95.5) | 172 (55.0) | 268 (86.2) | 85 (27.3) |
| Diarrhea | 60 (19.2) | 7 (2.2) | 138 (44.1) | 29 (9.3) | 103 (33.1) | 19 (6.1) |
| Fatigue | 107 (34.2) | 4 (1.3) | 110 (35.1) | 13 (4.2) | 87 (28.0) | 3 (1.0) |
| Pruritus | 59 (18.8) | 0 | 104 (33.2) | 6 (1.9) | 110 (35.4) | 1 (0.3) |
| Rash | 81 (25.9) | 2 (0.6) | 126 (40.3) | 15 (4.8) | 102 (32.8) | 6 (1.9) |
| Nausea | 41 (13.1) | 0 | 81 (25.9) | 7 (2.2) | 50 (16.1) | 2 (0.6) |
| Pyrexia | 18 (5.8) | 0 | 58 (18.5) | 2 (0.6) | 21 (6.8) | 1 (0.3) |
| Decreased appetite | 34 (10.9) | 0 | 56 (17.9) | 4 (1.3) | 39 (12.5) | 1 (0.3) |
| Increase in alanine aminotransferase | 12 (3.8) | 4 (1.3) | 55 (17.6) | 26 (8.3) | 12 (3.9) | 5 (1.6) |
| Vomiting | 20 (6.4) | 1 (0.3) | 48 (15.3) | 8 (2.6) | 23 (7.4) | 1 (0.3) |
| Increase in aspartate aminotransferase | 12 (3.8) | 3 (1.0) | 48 (15.3) | 19 (6.1) | 11 (3.5) | 2 (0.6) |
| Hypothyroidism | 27 (8.6) | 0 | 47 (15.0) | 1 (0.3) | 13 (4.2) | 0 |
| Colitis | 4 (1.3) | 2 (0.6) | 37 (11.8) | 24 (7.7) | 36 (11.6) | 27 (8.7) |
| Arthralgia | 24 (7.7) | 0 | 33 (10.5) | 1 (0.3) | 19 (6.1) | 0 |
| Headache | 23 (7.3) | 0 | 32 (10.2) | 1 (0.3) | 24 (7.7) | 1 (0.3) |
| Dyspnea | 14 (4.5) | 1 (0.3) | 32 (10.2) | 2 (0.6) | 13 (4.2) | 0 |
| Treatment-related adverse event leading to discontinuation | 24 (7.7) | 16 (5.1) | 114 (36.4) | 92 (29.4) | 46 (14.8) | 41 (13.2) |

*The severity of adverse events was graded according to the National Cancer Institute Common Terminology Criteria for Adverse Events, version 4.0.
[†]The treatment-related adverse events listed here were reported in at least 10% of the patients in any of the three study groups.

TABLE 6

Treatment-related Select Adverse Events (Safety Population).*

| Event | Nivolumab alone (N = 313) | | Nivolumab plus Ipilimumab (N = 313) | | Ipilimumab alone (N = 311) | |
|---|---|---|---|---|---|---|
| | Total | Grade 3 or 4 | Total | Grade 3 or 4 | Total | Grade 3 or 4 |
| | no. of patients with event (%) | | | | | |
| Any select adverse event | 194 (62.0) | 24 (7.7) | 275 (87.9) | 124 (39.6) | 229 (73.6) | 58 (18.6) |
| Treatment-related select adverse event† | | | | | | |
| Skin | 131 (41.9) | 5 (1.6) | 185 (59.1) | 18 (5.8) | 168 (54.0) | 9 (2.9) |
| Pruritus | 59 (18.8) | 0 | 104 (33.2) | 6 (1.9) | 110 (35.4) | 1 (0.3) |
| Rash | 68 (21.7) | 1 (0.3) | 89 (28.4) | 9 (2.9) | 65 (20.9) | 5 (1.6) |
| Rash maculo-papular | 13 (4.2) | 1 (0.3) | 37 (11.8) | 6 (1.9) | 37 (11.9) | 1 (0.3) |
| Vitiligo | 23 (7.3) | 1 (0.3) | 21 (6.7) | 0 | 12 (3.9) | 0 |
| Gastrointestinal | 61 (19.5) | 7 (2.2) | 145 (46.3) | 46 (14.7) | 114 (36.7) | 36 (11.6) |
| Diarrhea | 60 (19.2) | 7 (2.2) | 138 (44.1) | 29 (9.3) | 103 (33.1) | 19 (6.1) |
| Colitis | 4 (1.3) | 2 (0.6) | 37 (11.8) | 24 (7.7) | 36 (11.6) | 27 (8.7) |
| Hepatic | 20 (6.4) | 8 (2.6) | 94 (30.0) | 59 (18.8) | 22 (7.1) | 5 (1.6) |
| Increase in alanine aminotransferase | 12 (3.8) | 4 (1.3) | 55 (17.6) | 26 (8.3) | 12 (3.9) | 5 (1.6) |
| Increase in aspartate aminotransferase | 12 (3.8) | 3 (1.0) | 48 (15.3) | 19 (6.1) | 11 (3.5) | 2 (0.6) |
| Endocrine | 45 (14.4) | 2 (0.6) | 94 (30.0) | 15 (4.8) | 34 (10.9) | 7 (2.3) |
| Hypothyroidism | 27 (8.6) | 0 | 47 (15.0) | 1 (0.3) | 13 (4.2) | 0 |
| Hyperthyroidism | 13 (4.2) | 0 | 31 (9.9) | 3 (1.0) | 3 (1.0) | 0 |
| Hypophysitis | 2 (0.6) | 1 (0.3) | 24 (7.7) | 5 (1.6) | 12 (3.9) | 6 (1.9) |
| Pulmonary | 5 (1.6) | 1 (0.3) | 22 (7.0) | 3 (1.0) | 6 (1.9) | 1 (0.3) |
| Pneumonitis | 4 (1.3) | 1 (0.3) | 20 (6.4) | 3 (1.0) | 5 (1.6) | 1 (0.3) |

*The severity of adverse events was graded according to the National Cancer Institute Common Terminology Criteria for Adverse Events, version 4.0.
†The treatment-related select adverse events listed here were reported in at least 5% of the patients in any of the three study groups.

TABLE 7

Management of Treatment-related Select Adverse Events With Immune Modulatory Medication (IMM).

| Select Adverse Event Organ Category | Nivolumab | | | Nivolumab plus Ipilimumab | | | Ipilimumab | | |
|---|---|---|---|---|---|---|---|---|---|
| | Patients managed with IMM, n (%) | Patients with resolution of AE after treatment with IMM, n (%) | Median time to resolution, weeks (95% CI) | Patients managed with IMM, n (%) | Patients with resolution of AE after treatment with IMM, n (%) | Median time to resolution, weeks (95% CI) | Patients managed with IMM, n (%) | Patients with resolution of AE after treatment with IMM, n (%) | Median time to resolution, weeks (95% CI) |
| Skin | 33/131 (25.2) | 17 (54.8) | 34.9 (18.0, NE) | 80/185 (43.2) | 55 (75.3) | 8.6 (7.0, 12.6) | 58/168 (34.5) | 41 (74.5) | 12.4 (8.9, 19.1) |
| Grade 3-4 | 3/5 (60.0) | 3 (75.0) | 2.1 (0.9, NE) | 12/18 (66.7) | 12 (85.7) | 3.4 (1.1, 12.4) | 5/9 (55.6) | 5 (83.3) | 6.1 (4.4, NE) |
| Gastro-intestinal | 9/61 (14.8) | 5 (71.4) | 4.0 (0.8, NE) | 71/145 (49.0) | 62 (93.9) | 4.5 (3.5, 5.7) | 54/114 (47.4) | 44 (88.0) | 4.9 (2.9, 7.6) |
| Grade 3-4 | 5/7 (71.4) | 3 (50.0) | NE (0.8, NE) | 41/46 (89.1) | 41 (97.6) | 3.0 (1.9, 4.3) | 33/36 (91.7) | 31 (88.6) | 4.7 (1.9, 6.1) |
| Endocrine | 5/45 (11.1) | 2 (40.0) | 24.3 (7.1, NE) | 36/94 (38.3) | 14 (41.2) | NE (10.4, NE) | 15/34 (44.1) | 4 (28.6) | NE (0.71, NE) |
| Grade 3-4 | 2/2 (100) | 0 | NE (NE, NE) | 10/15 (66.7) | 5 (45.5) | NE (4.5, NE) | 7/7 (100.0) | 3 (42.9) | NE (0.43, NE) |
| Hepatic | 8/22 (36.4) | 6 (100.0) | 7.0 (2.0, 27.1) | 46/95 (48.4) | 43 (95.6) | 5.9 (3.3, 6.6) | 3/22 (13.6) | 3 (100.0) | 4.1 (4.0, 7.7) |
| Grade 3-4 | 7/8 (87.5) | 6 (100.0) | 7.0 (2.0, 27.1) | 37/60 (61.7) | 38 (100.0) | 4.1 (3.0, 6.1) | 2/5 (40.0) | 2 (100.0) | 5.9 (4.0, 7.7) |
| Pulmonary | 4/5 (80.0) | 4 (100.0) | 3.3 (2.3, 9.1) | 17/22 (77.3) | 16 (94.1) | 6.1 (1.1, 8.3) | 3/6 (50.0) | 2 (66.7) | 6.1 (6.0, 6.3) |
| Grade 3-4 | 1/1 (100) | 1 (100.0) | 2.3 (NE, NE) | 2/3 (66.7) | 2 (100.0) | 4.2 (1.1, 7.3) | 1/1 (100) | 1 (100.0) | 4.7 (NE, NE) |
| Renal | 1/3 (33.3) | 1 (100.0) | 0.3 (NE, NE) | 4/17 (23.5) | 3 (100.0) | 1.7 (0.4, 3.7) | 3/8 (37.5) | 3 (100.0) | 4.6 (0.6, 16.1) |
| Grade 3-4 | 0/1 | 0 | — | 3/6 (50.0) | 3 (100.0) | 1.7 (0.4, 3.6) | 1/1 (100) | 1 (100.0) | 4.6 (NE, NE) |

The median progression-free survival reported for the combination of nivolumab and ipilimumab in this study (11.7 months in BRAF-mutant patients) is similar to that recently reported for the combination of BRAF and MEK inhibition in BRAF-mutant metastatic melanoma (9.9 months for vemurafenib and cobimetinib; 9.3 to 11.4 months for dabrafenib and trametinib). Resistance to such targeted therapies is almost inevitable when used as monotherapy and in many cases is very rapid. The confirmed rate of objective response for combined nivolumab and ipilimumab (57.6%) is numerically higher than observed with PD-1 blockade alone in advanced melanoma (nivolumab [40%] in treatment-naïve patients with wild-type BRAF or pembrolizumab [37%] in ipilimumab-naïve patients).

The results of subgroup analyses suggest that the greatest benefit for the combination of nivolumab and ipilimumab versus nivolumab alone may occur in the setting of negative PD-L1 tumor expression. In the PD-L1-positive group, both nivolumab alone and nivolumab plus ipilimumab resulted in a similar prolongation of progression-free survival as compared with ipilimumab alone, although objective response rates were numerically higher in the combination group versus either nivolumab or ipilimumab alone. Thus, the use of PD-L1 as a biomarker may allow clinicians to make more informed decisions about the risk-benefit of combination therapy versus monotherapy. Nonetheless, the observation of at least additive activity of the combination of ipilimumab and nivolumab in the setting of negative PD-L1 expression is of interest in melanoma as well as in other tumor types in which PD-1 checkpoint inhibitors are under evaluation.

The incidence of adverse events in this study was, in general, lowest in the nivolumab group and highest in the combination group. The overall incidence of grade 3 or 4 drug-related adverse events was higher in the combination group as compared with ipilimumab alone (39.6% versus 18.6%), as a result of a slightly higher incidence in most adverse events, particularly hepatic toxicity, where the rates of grade 3 or 4 ALT/AST elevations were 6-8% for the combination and approximately 1% for ipilimumab alone. One drug-related death was reported in each of the nivolumab and ipilimumab groups but none in the combination group. Overall, the safety profile of the combination of nivolumab and ipilimumab was consistent with previous experience with nivolumab or ipilimumab alone. No new safety signals were identified, and adverse events were manageable with established treatment guidelines as most select adverse events resolved with immune modulatory agents. These data suggest that the combination of nivolumab and ipilimumab can be used safely in a broad range of clinical settings.

In summary, the report shows increased progression-free survival and objective response rates for nivolumab alone and the combination of nivolumab and ipilimumab, as compared with ipilimumab alone, in previously untreated advanced melanoma. Adverse events with the combination were managed with established algorithms, with no study drug-related deaths. Overall, nivolumab alone and the combination of nivolumab and ipilimumab are promising treatment options for previously untreated advanced melanoma.

---

SEQUENCES $V_H$ amino acid sequence of 28-8 (*Oryctolagus cuniculus*)

(SEQ ID NO: 1)

Met Glu Thr Gly Leu Arg Trp Leu Leu Leu Val Ala

Val Leu Lys Gly Val Gln Cys Leu Ser Val Glu Glu

Ser Gly Gly Arg Leu Val Thr Pro Gly Thr Pro Leu

-continued

---

SEQUENCES

---

Thr Leu Thr Cys Thr Ala Ser Gly Phe Thr Ile Thr

Asn Tyr His Met Phe Trp Val Arg Gln Ala Pro Gly

Lys Gly Leu Glu Trp Ile Gly Val Ile Thr Ser Ser

Gly Ile Gly Ser Ser Ser Thr Thr Tyr Tyr Ala Thr

Trp Ala Lys Gly Arg Phe Thr Ile Ser Lys Thr Ser

Thr Thr Val Asn Leu Arg Ile Thr Ser Pro Thr Thr

Glu Asp Thr Ala Thr Tyr Phe Cys Ala Arg Asp Tyr

Phe Thr Asn Thr Tyr Tyr Ala Leu Asp Ile Trp Gly

Pro Gly Thr Leu Val Thr Val Ser Ser $V_L$ amino acid sequence of 28-8 (*Oryctolagus cuniculus*)

(SEQ ID NO: 2)

Met Asp Thr Arg Ala Pro Thr Gln Leu Leu Gly Leu

Leu Leu Leu Trp Leu Pro Gly Ala Arg Cys Ala Leu

Val Met Thr Gln Thr Pro Ser Ser Thr Ser Thr Ala

Val Gly Gly Thr Val Thr Ile Lys Cys Gln Ala Ser

Gln Ser Ile Ser Val Tyr Leu Ala Trp Tyr Gln Gln

Lys Pro Gly Gln Pro Pro Lys Leu Leu Ile Tyr Ser

Ala Ser Thr Leu Ala Ser Gly Val Pro Ser Arg Phe

Lys Gly Ser Arg Ser Gly Thr Glu Tyr Thr Leu Thr

Ile Ser Gly Val Gln Arg Glu Asp Ala Ala Thr Tyr

Tyr Cys Leu Gly Ser Ala Gly Ser

Heavy Chain CDR1 sequence of 28-8 (*Oryctolagus cuniculus*)

(SEQ ID NO: 3)

Asn Tyr His Met Phe

Heavy Chain CDR2 sequence of 28-8 (*Oryctolagus cuniculus*)

(SEQ ID NO: 4)

Val Ile Thr Ser Ser Gly Ile Gly Ser Ser Ser Thr

Thr Tyr Tyr Ala Thr Trp Ala Lys Gly

Heavy Chain CDR3 sequence of 28-8 (*Oryctolagus cuniculus*)

(SEQ ID NO: 5)

Asp Tyr Phe Thr Asn Thr Tyr Tyr Ala Leu Asp Ile

Light Chain CDR1 sequence of 28-8 (*Oryctolagus cuniculus*)

(SEQ ID NO: 6)

Gln Ala Ser Gln Ser Ile Ser Val Tyr Leu Ala

Light Chain CDR2 sequence of 28-8 (*Oryctolagus cuniculus*)

(SEQ ID NO: 7)

Ser Ala Ser Thr Leu Ala Ser

Light Chain CDR3 sequence of 28-8 (*Oryctolagus cuniculus*)

(SEQ ID NO: 8)

Leu Gly Ser Ala Gly Ser Asp Asp Ala Ala

What is claimed is:

1. A method for treating a melanoma tumor in a patient in need thereof comprising:

(i) identifying a patient having a PD-L1 positive melanoma tumor, wherein the PD-L1 positive melanoma tumor is characterized by at least about 5% of tumor cells expressing PD-L1 in a test tissue sample obtained from the patient, the test tissue sample comprising tumor cells and/or tumor-infiltrating inflammatory cells; and (ii) administering to the patient a flat dose of 480 mg of nivolumab or an antigen-binding portion thereof that binds specifically to a human PD-1 once every four weeks, without regard for the weight or body surface area (BSA) of the patient, wherein the patient is not administered a combination of nivolumab or an antigen-binding portion thereof and another anti-cancer agent.

2. The method of claim 1, wherein the patient is characterized by (i) extended progression-free survival for over 12 months following the administration, (ii) tumor size reduction at least about 10% compared to the tumor size prior to the administration, or (iii) both (i) and (ii).

3. The method of claim 1, wherein the test tissue sample is a formalin-fixed paraffin-embedded (FFPE) tissue sample.

4. The method of claim 1, wherein the expression of PD-L1 is determined using an automated IHC assay.

5. The method of claim 4, wherein the IHC assay is performed using an anti-PD-L1 monoclonal antibody that specifically binds to the PD-L1 and wherein the anti-PD-L1 monoclonal antibody comprises a heavy chain CDR1 comprising the amino acid sequence set forth in SEQ ID NO: 3, a heavy chain CDR2 comprising the amino acid sequence set forth in SEQ ID NO: 4, a heavy chain CDR3 comprising the amino acid sequence set forth in SEQ ID NO: 5, a light chain CDR1 comprising the amino acid sequence set forth in SEQ ID NO: 6, a light chain CDR2 comprising the amino acid sequence set forth in SEQ ID NO: 7, and a light chain CDR3 comprising the amino acid sequence set forth in SEQ ID NO: 8.

6. A method for treating a melanoma tumor in a patient in need thereof comprising administering to the patient a flat dose of 480 mg of nivolumab or an antigen-binding portion thereof that binds specifically to a human PD-1 once every four weeks, without regard for the weight or body surface area (BSA) of the patient, wherein the patient is not administered a combination of nivolumab or an antigen-binding portion thereof and another anti-cancer agent, wherein the patient is identified as having a PD-L1 positive melanoma tumor prior to the administration, wherein the PD-L1 positive melanoma tumor is characterized by at least about 5% of tumor cells expressing PD-L1 in a test tissue sample obtained from the patient, the test tissue sample comprising tumor cells and/or tumor-infiltrating inflammatory cells.

7. The method of claim 6, wherein the patient is characterized by (i) extended progression-free survival for over 12 months following the administration, (ii) tumor size reduction at least about 10% compared to the tumor size prior to the administration, or (iii) both (i) and (ii).

8. The method of claim 6, wherein the test tissue sample is a formalin-fixed paraffin-embedded (FFPE) tissue sample.

9. The method of claim 8, wherein the expression of PD-L1 is determined using an automated IHC assay.

10. The method of claim 9, wherein the IHC assay is performed using an anti-PD-L1 monoclonal antibody that specifically binds to the PD-L1 and wherein the anti-PD-L1 monoclonal antibody comprises a heavy chain CDR1 comprising the amino acid sequence set forth in SEQ ID NO: 3, a heavy chain CDR2 comprising the amino acid sequence set forth in SEQ ID NO: 4, a heavy chain CDR3 comprising the amino acid sequence set forth in SEQ ID NO: 5, a light chain CDR1 comprising the amino acid sequence set forth in SEQ ID NO: 6, a light chain CDR2 comprising the amino acid sequence set forth in SEQ ID NO: 7, and a light chain CDR3 comprising the amino acid sequence set forth in SEQ ID NO: 8.

* * * * *

SEQUENCE LISTING

<160> NUMBER OF SEQ ID NOS: 8

<210> SEQ ID NO 1
<211> LENGTH: 141
<212> TYPE: PRT
<213> ORGANISM: Oryctolagus cuniculus

<400> SEQUENCE: 1

```
Met Glu Thr Gly Leu Arg Trp Leu Leu Leu Val Ala Val Leu Lys Gly
1               5                   10                  15

Val Gln Cys Leu Ser Val Glu Glu Ser Gly Gly Arg Leu Val Thr Pro
            20                  25                  30

Gly Thr Pro Leu Thr Leu Thr Cys Thr Ala Ser Gly Phe Thr Ile Thr
            35                  40                  45

Asn Tyr His Met Phe Trp Val Arg Gln Ala Pro Gly Lys Gly Leu Glu
        50                  55                  60

Trp Ile Gly Val Ile Thr Ser Ser Gly Ile Gly Ser Ser Ser Thr Thr
65                  70                  75                  80

Tyr Tyr Ala Thr Trp Ala Lys Gly Arg Phe Thr Ile Ser Lys Thr Ser
                85                  90                  95

Thr Thr Val Asn Leu Arg Ile Thr Ser Pro Thr Thr Glu Asp Thr Ala
            100                 105                 110

Thr Tyr Phe Cys Ala Arg Asp Tyr Phe Thr Asn Thr Tyr Tyr Ala Leu
            115                 120                 125

Asp Ile Trp Gly Pro Gly Thr Leu Val Thr Val Ser Ser
    130                 135                 140
```

<210> SEQ ID NO 2
<211> LENGTH: 116
<212> TYPE: PRT
<213> ORGANISM: Oryctolagus cuniculus

<400> SEQUENCE: 2

```
Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ser Ser
            20                  25                  30

Thr Ser Thr Ala Val Gly Gly Thr Val Thr Ile Lys Cys Gln Ala Ser
            35                  40                  45

Gln Ser Ile Ser Val Tyr Leu Ala Trp Tyr Gln Gln Lys Pro Gly Gln
        50                  55                  60

Pro Pro Lys Leu Leu Ile Tyr Ser Ala Ser Thr Leu Ala Ser Gly Val
65                  70                  75                  80

Pro Ser Arg Phe Lys Gly Ser Arg Ser Gly Thr Glu Tyr Thr Leu Thr
                85                  90                  95

Ile Ser Gly Val Gln Arg Glu Asp Ala Ala Thr Tyr Tyr Cys Leu Gly
            100                 105                 110

Ser Ala Gly Ser
        115
```

<210> SEQ ID NO 3
<211> LENGTH: 5
<212> TYPE: PRT
<213> ORGANISM: Oryctolagus cuniculus

<400> SEQUENCE: 3

```
Asn Tyr His Met Phe
1               5
```

-continued

```
<210> SEQ ID NO 4
<211> LENGTH: 21
<212> TYPE: PRT
<213> ORGANISM: Oryctolagus cuniculus

<400> SEQUENCE: 4

Val Ile Thr Ser Ser Gly Ile Gly Ser Ser Ser Thr Thr Tyr Tyr Ala
1               5                   10                  15

Thr Trp Ala Lys Gly
            20

<210> SEQ ID NO 5
<211> LENGTH: 12
<212> TYPE: PRT
<213> ORGANISM: Oryctolagus cuniculus

<400> SEQUENCE: 5

Asp Tyr Phe Thr Asn Thr Tyr Tyr Ala Leu Asp Ile
1               5                   10

<210> SEQ ID NO 6
<211> LENGTH: 11
<212> TYPE: PRT
<213> ORGANISM: Oryctolagus cuniculus

<400> SEQUENCE: 6

Gln Ala Ser Gln Ser Ile Ser Val Tyr Leu Ala
1               5                   10

<210> SEQ ID NO 7
<211> LENGTH: 7
<212> TYPE: PRT
<213> ORGANISM: Oryctolagus cuniculus

<400> SEQUENCE: 7

Ser Ala Ser Thr Leu Ala Ser
1               5

<210> SEQ ID NO 8
<211> LENGTH: 10
<212> TYPE: PRT
<213> ORGANISM: Oryctolagus cuniculus

<400> SEQUENCE: 8

Leu Gly Ser Ala Gly Ser Asp Asp Ala Ala
1               5                   10
```